US008299899B2

(12) United States Patent
Frysz et al.

(10) Patent No.: US 8,299,899 B2
(45) Date of Patent: *Oct. 30, 2012

(54) AIMD EXTERNAL PROGRAMMER INCORPORATING A MULTIFUNCTION RFID READER HAVING A LIMITED TRANSMIT TIME AND A TIME-OUT PERIOD

(75) Inventors: Christine A. Frysz, Orchard Park, NY (US); Robert A. Stevenson, Canyon Country, CA (US); Geddes Frank Tyers, Vancouver (CA)

(73) Assignee: Greatbatch Ltd., Clarence, NY (US)

( * ) Notice: Subject to any disclaimer, the term of this patent is extended or adjusted under 35 U.S.C. 154(b) by 78 days.

This patent is subject to a terminal disclaimer.

(21) Appl. No.: 12/874,097

(22) Filed: Sep. 1, 2010

(65) Prior Publication Data
US 2010/0328049 A1 Dec. 30, 2010

Related U.S. Application Data

(63) Continuation-in-part of application No. 12/566,490, filed on Sep. 24, 2009.

(60) Provisional application No. 61/240,864, filed on Sep. 9, 2009, provisional application No. 61/116,094, filed on Nov. 19, 2008.

(51) Int. Cl.
*H04Q 5/22* (2006.01)

(52) U.S. Cl. ............ 340/10.1; 340/10.2; 340/10.3; 340/10.31; 340/10.32; 340/10.33; 340/10.34; 340/10.4; 340/10.41; 340/10.42; 340/10.5; 340/10.51; 340/10.52; 340/10.6

(58) Field of Classification Search ........ 340/10.1–10.6, 340/572.1–572.9
See application file for complete search history.

(56) References Cited

U.S. PATENT DOCUMENTS

| | | | | |
|---|---|---|---|---|
| 3,469,191 A | * | 9/1969 | Russell, Jr. et al. | 455/115.4 |
| 3,500,458 A | * | 3/1970 | Cannalte | 455/115.4 |
| 3,500,459 A | * | 3/1970 | Battin et al. | 455/78 |
| 4,688,213 A | * | 8/1987 | Raychaudhuri | 370/348 |
| 4,839,642 A | * | 6/1989 | Batz et al. | 340/10.31 |
| 5,340,361 A | * | 8/1994 | Sholder | 607/24 |
| 5,423,334 A | * | 6/1995 | Jordan | 128/899 |
| 7,173,920 B2 | * | 2/2007 | Moulsley | 370/335 |
| 7,346,120 B2 | * | 3/2008 | McCorkle | 375/295 |
| 7,383,033 B2 | * | 6/2008 | Holger | 455/264 |
| 7,406,349 B2 | * | 7/2008 | Seeberger et al. | 607/30 |
| 7,773,691 B2 | * | 8/2010 | Khlat et al. | 375/296 |
| 7,826,438 B1 | * | 11/2010 | Salhotra et al. | 370/345 |
| 2001/0045883 A1 | * | 11/2001 | Holdaway et al. | 340/5.51 |

(Continued)

FOREIGN PATENT DOCUMENTS

JP 56122247 A * 9/1981

(Continued)

*Primary Examiner* — George A Bugg
*Assistant Examiner* — Paul Obiniyi
(74) *Attorney, Agent, or Firm* — Michael F. Scalise

(57) ABSTRACT

A system is provided for identifying implanted medical devices, leads and systems, as well as objects in close proximity to a patient having an implanted medical device (IMD), using a radio frequency identification (RFID) tag having retrievable information relating to the IMD, lead system and/or patient. An RFID tag communicator includes a circuit for limiting the total continuous transmit time of an interrogation signal, and a time-out circuit for delaying a second and any subsequent interrogation of the RFID tag. An external IMD programmer incorporating a multi-functional RFID reader is capable of identifying and communicating with various types of implanted medical devices, even if such devices are made by different manufacturers.

43 Claims, 24 Drawing Sheets

U.S. PATENT DOCUMENTS

| | | | |
|---|---|---|---|
| 2003/0174048 A1* | 9/2003 | McCorkle | 340/10.34 |
| 2004/0030260 A1* | 2/2004 | Arx | 600/549 |
| 2005/0063488 A1* | 3/2005 | Troyk et al. | 375/316 |
| 2005/0188277 A1* | 8/2005 | Tayler et al. | 714/39 |
| 2005/0195643 A1* | 9/2005 | Holger | 365/154 |
| 2005/0247319 A1* | 11/2005 | Berger | 128/898 |
| 2005/0258242 A1* | 11/2005 | Zarembo | 235/385 |
| 2006/0050638 A1 | 3/2006 | Meyer et al. | |
| 2006/0076401 A1* | 4/2006 | Frerking | 235/380 |
| 2006/0116744 A1* | 6/2006 | Von Arx et al. | 607/60 |
| 2006/0212096 A1* | 9/2006 | Stevenson | 607/60 |
| 2006/0247684 A1 | 11/2006 | Halperin et al. | |
| 2007/0112398 A1 | 5/2007 | Stevenson et al. | |
| 2007/0167994 A1* | 7/2007 | Shelton et al. | 607/60 |
| 2007/0210923 A1* | 9/2007 | Butler et al. | 340/572.8 |
| 2008/0041929 A1* | 2/2008 | Bauman et al. | 235/375 |
| 2008/0048855 A1* | 2/2008 | Berger | 340/539.12 |
| 2008/0065181 A1* | 3/2008 | Stevenson | 607/115 |
| 2009/0009336 A1* | 1/2009 | Ishikawa | 340/572.7 |
| 2010/0007467 A1* | 1/2010 | Breitfuss et al. | 340/10.1 |
| 2010/0060431 A1* | 3/2010 | Stevenson et al. | 340/10.1 |
| 2010/0085160 A1* | 4/2010 | Fu | 340/10.1 |
| 2010/0106224 A1* | 4/2010 | Von Arx et al. | 607/60 |
| 2010/0123547 A1* | 5/2010 | Stevenson et al. | 340/5.61 |
| 2010/0152816 A1* | 6/2010 | Von Arx et al. | 607/60 |
| 2010/0161003 A1* | 6/2010 | Malmberg et al. | 607/60 |
| 2010/0185263 A1* | 7/2010 | Stevenson et al. | 607/60 |
| 2011/0029043 A1* | 2/2011 | Frysz et al. | 607/60 |

FOREIGN PATENT DOCUMENTS

| | | | |
|---|---|---|---|
| JP | 356122247 | * | 9/1981 |
| JP | 61244149 A | * | 10/1986 |
| JP | 361244149 | * | 10/1986 |
| JP | 07221664 A | * | 8/1995 |

* cited by examiner

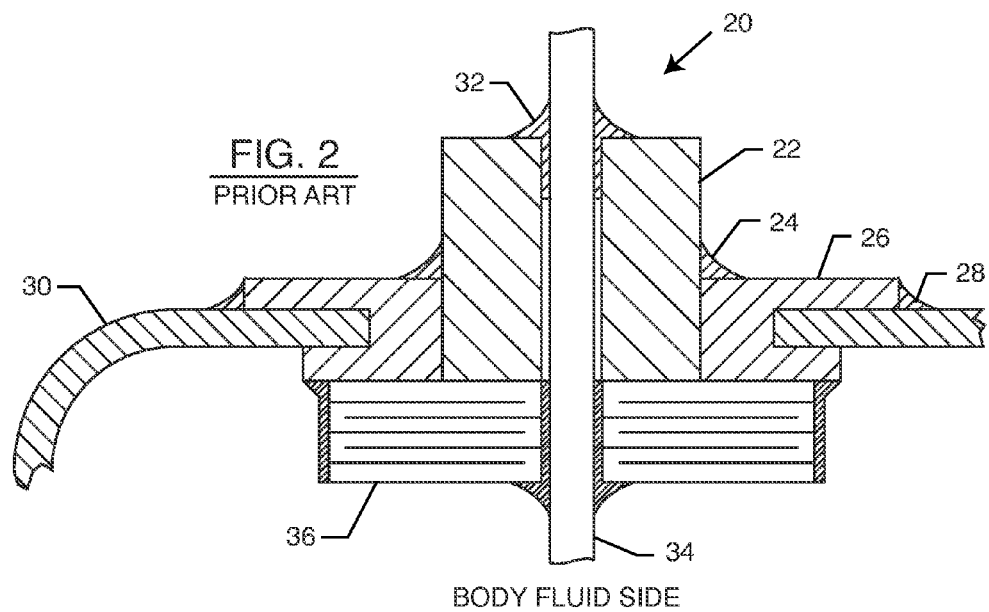
FIG. 2
PRIOR ART
BODY FLUID SIDE
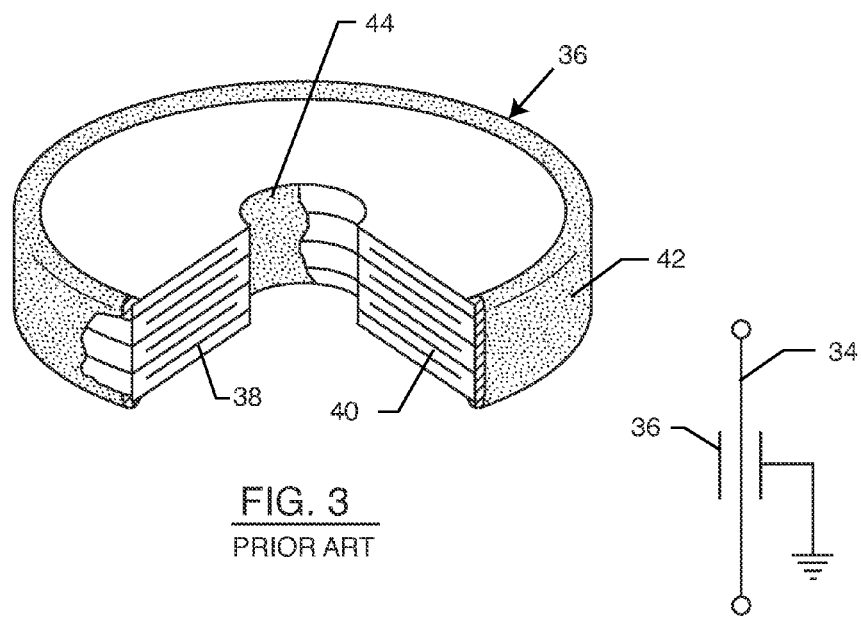
FIG. 3
PRIOR ART
FIG. 4
PRIOR ART RFID Readers Tested by FDA

| RFID Equipment Code | RFID Antenna Configuration (cm) | Governing Standard | Carrier Frequency (MHz) | Max field intensity (A/m Peak @ 2.5 cm) | RF Usage | | | |
|---|---|---|---|---|---|---|---|---|
| | | | | | Pulse Format | Pulse Repetition Rate (Hz) | Duty Factor | Pulse Width (ms) |
| 1 | Loop 85 x 50 | ISO 11785 | 0.134 | 68 | CW | | | |
| 2 | Loop 85 x 50 | ISO 11785 | 0.134 | 162 | SEQ | 14.3 | 0.72 | 49.9 |
| 3 | Loop 20 x 20 | ISO 11785 | 0.134 | 269 | SEQ | 10.7 | 0.54 | 50.3 |
| 4 | Loop 20 x 20 | ISO 11785 | 0.134 | 267 | SEQ | 7 | 0.69 | 97.8 |
| 5 | Loop 20 x 20 | ISO 11785 | 0.134 | 258 | SEQ | 25.8 | 0.42 | 16.4 |
| 6 | Loop 31 x 31 | ISO 18000 3 mode 1 | 13.56 | 4.6 | | 10.9 | 0.11 | 10.3 |
| 7 | Loop 20 x 20 | ISO 18000 3 mode 1 | 13.56 | 4.9 | | 4 | 0.13 | 31.9 |
| 8 | Loop 31 x 31 | ISO 18000 3 mode 1 | 13.56 | 8.6 | CW | | | |
| 9 | Loop 31 x 31 | ISO 18000 3 mode 1 | 13.56 | 8.7 | Full Duplex | 0.9 | 1.0 | 1070 |
| 10 | Loop 31 x 31 | ISO 18000 3 mode 1 | 13.56 | 8.8 | Full Duplex | 11.1 | 1.0 | 90 |
| 11 | Handheld | ISO 18000 3 mode 1 | 13.56 | 7.8 | | 3.5 | 0.92 | 264.0 |
| 12 | XRAY Needed | ISO 18000-6c | 915 | -- | | 56100 | 0.72 | 0.01 |
| 13 | XRAY Needed | ISO 18000-6c | 915 | -- | | NA | NA | NA |

FIG. 7

2006 and 2008 FDA TESTS

| 2006 | 2008 |
|---|---|
| • 22 Pacemakers<br>• 19 ICDs<br>• 7 RFID Systems<br>  - Two 134 kHz Systems<br>  - Four 13.56 MHz Systems<br>  - One 915 MHz Systems | • 15 Pacemakers<br>• 15 ICDs<br>• 13 RFID Systems<br>  - Five 134 kHz Systems<br>  - Six 13.56 MHz Systems<br>  - Two 915 MHz Systems |

FIG. 8

Maximum Recorded Threshold Distances of Reactions

- Pacemaker
  - Any Response
    - 60 cm (occasional atrial and ventricular pacing) LF
    - 22.5 cm (occasional ventricular pacing) HF
  - Class I Reaction (total atrial and ventricular inhibition)
    - 40 cm LF
    - 20 cm HF
- ICD
  - Any Response
    - 40 cm (occasional atrial inhibition) LF
    - 22.5 cm (occasional atrial inhibition) HF
  - Class I Response (inappropriate high voltage shock)
    - 12.5 cm LF
    - No Class 1 Reactions at HF

FIG. 27

AIMD EXTERNAL PROGRAMMER INCORPORATING A MULTIFUNCTION RFID READER HAVING A LIMITED TRANSMIT TIME AND A TIME-OUT PERIOD

FIELD OF THE INVENTION

The present invention relates to design modifications to prior art or newly designed active implantable medical device (AIMD) external programmers. More particularly, the present invention relates to an AIMD external telemetry programmer that incorporates an RFID reader or reader/interrogator/transceiver, for display of information stored on an RFID tag relating to the implanted medical device and/or leads implanted in a patient or information about the patient, and for optionally inserting new, corrected or additional information onto the RFID tag. The novel RFID interrogation system to be associated with the AIMD external telemetry programmer includes a circuit for limiting the total continuous transmit time of an electromagnetic signal and a time-out circuit for delaying a subsequent transmission of the electromagnetic signal.

BACKGROUND OF THE INVENTION

The RFID reader industry has literally been exploding over the last few years with new applications and indications being discovered on what sometimes almost seems a daily basis. For example, RFID readers and their associated tags are being used for inventory tracking, pharmaceutical tracking, tracking of patients in hospitals, automated checkout in super markets of a basket full of goods with associated RFID tags, automobile keyless entry systems and keyless ignition systems, operating room sponge detector systems, and identification of patient RFID wrist bands. There are several main frequency bands that are now dominating the worldwide RFID industry. Four of the popular ones are low frequency (LF) which generally ranges from 125 to 150 kHz, high frequency (HF) which is at 13.56 MHz, very high frequency (VHF) which is at 433 MHz, and ultra high frequency (UHF) which generally operates at 915 MHz. Moreover, there are both national (American) and international standards (ISO) defining the modulation protocols and pulse widths and repetition rates so that standardized RFID tags can be read by a wide variety of readers. In fact, many readers transmit over a broad range of the RFID protocols for this exact reason. With the explosion of RFID emitters (readers also known as interrogators and sometimes referred to herein as communicators), patients with passive or active (electronic) medical devices (PMDs or AMDs) are increasingly running the risk of inadvertently coming in close proximity to such RFID emitters. AMDs can also be implanted inside (or partially inside) the human body and are known as active implantable medical devices (AIMDs).

FIG. 1 is a wire formed diagram of a generic human body. Various locations are shown for active, passive, structural and other implantable and external medical devices 10 that are currently in use, and in which the present invention may find application. 10A represents a family of external and implantable hearing devices which can include the group of hearing aids, cochlear implants, piezoelectric sound bridge transducers and the like. 10B includes an entire variety of neurostimulators and brain stimulators, and hydrocephalic fluid pumps, drug and hormone insulin injection administration devices, etc. Neurostimulators are used, for example, to stimulate the Vagus nerve to treat epilepsy, obesity, Parkinsonism and depression. Brain stimulator systems are similar to a pacemaker-like pulse generator and include leads leading to electrodes implanted deep into the brain. 10C shows a cardiac pacemaker which is well-known in the art. 10D includes the various types of left ventricular assist devices (LVAD's), and artificial hearts, for example, the recently introduced centrifugal empowered devices. 10E includes an entire family of drug pumps which can be used for dispensing of insulin, chemotherapy drugs, pain medications and the like. 10F includes a variety of external or implantable bone growth stimulators for rapid healing of fractures. 10G includes urinary and/or fecal incontinence devices. 10H includes the family of pain relief spinal cord stimulators and anti-tremor stimulators. 10H also includes an entire family of other types of neurostimulators used to block pain. 10I is representative of implantable cardioverter defibrillators (ICDs) including those with biventricular and multi-site synchronization capabilities for the treatment of congestive heart failure (CHF).

All of the prior art AIMDs described in FIG. 1 are generally designed to work with an external telemetry programmer. For example, the external telemetry programmer can be a simple device about the size of a garage door opener or smaller, that a patient may use to reprogram the energy output levels of his spinal cord stimulator. Or, in the case of a cardiac pacemaker or ICD, the external programmer would be the size of a rather large laptop computer often with a printer integrated within it for printing cardiac waveforms, and extensive digitalized data, and post market added patient identifiers and clinical information etc. In the case of a cardiac external programmer, it can be used to reprogram, for example, a pacemaker to different modes, to monitor pacemaker battery status, or even recover patient waveforms so a physician, during a patient follow-up visit, can make a diagnosis of a digitally interpreted arrhythmia that occurred weeks or even months previously. In the past, these prior art AIMD telemetry programmers were close-coupled, otherwise known as close-wanded telemetry. In this case, a magnetic loop antenna was connected by a cable to the external AIMD programmer. This external antenna looks somewhat like a hockey puck and is based on close-coupled magnetic coupling with a coil embedded within the AIMD. The more recent trend has been to RF distance telemetry. In this case, the AIMD has a telemetry receiver and an antenna which works at very high frequency. Whereas the old close-coupled telemetry systems generally operated in the kilohertz frequency range, these newer systems work in the hundreds of megahertz or even gigahertz frequency bands. The advantage of the new RF distance telemetry is that the interrogating antenna does not have to be set close to the patient's implanted AIMD. In most cases, a physician can use a distance RF telemetry programmer from a desk while interrogating the device of a patient sitting directly in front.

There are many potential benefits to being able to rapidly determine the specific model and serial number of all components of a medical device system after implantation, and/or additional related device or patient information. For example, product recalls are an increasingly complex and extensive problem, and the ability to rapidly identify the precise model and serial number of an implanted product may be lifesaving. With all present programmers, regardless of wand design, only pulse generator model and serial numbers are routinely available, yet the majority of recalls affect leads. Certainly some pacemaker and ICD products allow medical staff to enter lead and limited patient and clinical data into the pulse generators random access memory, but this is done inconsistently, and all the entered information is lost when the pulse generator is replaced. The inclusion of an RFID chip with critical identifying lead information including: company, model number, serial number and date of manufacture in the connector expansion of leads, and RFID reader capacity in future programmers will reliably and efficiently make lead data available to follow-up and emergency personnel whereas that is not the case currently or until the technology described herein becomes widely available.

Currently, most AIMD patients are asked to carry some sort of identification. This is often in the form of a card carried in the wallet or an ID bracelet indicating, for example, that the patient has a pacemaker of a certain model and serial number. However, such forms of identification are often missing or not up to date. In addition, manufacturers' databases and related patient cardiac rhythm management device (CRMD) system cards are frequently incomplete and/or inaccurate. It is quite common for a patient to be presented at the emergency room (ER) of a hospital without his or her wallet and without wearing any type of a pacemaker ID bracelet. In addition, there have been a number of situations where the patient (due to dementia or Alzheimer's, etc.) cannot clearly state that he or she even has an AIMD such as a pacemaker.

There are various alternate methods for identifying implanted medical devices. One such method is the use of X-ray identification tags encapsulated within header blocks of cardiac pacemakers or ICDs. Such X-ray identification tags can be read on an X-ray of the implanted device and provide very basic information to the physician. The information so provided is very limited due to space and typically includes only a manufacturer code and or the model number of only the pulse generator. In an emergency, the time delay to obtain X-ray films can also be problematic.

Oftentimes the ER physician will palpate the patient's chest and feel that there is an implanted device present. If the patient is comatose, has low blood pressure, or is in another form of cardiac distress, the ER physician is presented with a serious dilemma. At that moment, all that the ER physician knows is that the patient has some sort of an implanted medical device (IMD) in his or her body. It could be a pacemaker, a cardioverter defibrillator (ICD), a vagus nerve stimulator, a deep brain stimulator, or a variety of other therapeutic and/or monitoring devices. What happens next is both laborious and time consuming. The ER physician will have various manufacturers' external programmers transported from the hospital cardiology laboratory or elsewhere down to the ER. ER personnel will then try to interrogate the implantable medical device to see if they can determine what it is. For example, they might first try to use a Medtronic programmer to see if it is a Medtronic pacemaker or ICD. If unsuccessful, they might try a St. Jude, a Guidant, a Sorin, a Biotronik and then some other manufacturers' external device. If none of those programmers work, then the ER physician has to consider that the implanted device may be a neurostimulator and perhaps secure a Cyberonics or Neuropace programmer. It may also be that the telemetry programming wand is mal-positioned as this can be quite sensitive, or that the implanted device has failed, etc. And even once the correct programmer for the implanted pulse generator has been identified and obtained, no reliable information becomes available on the associated lead(s), adapter(s) etc. Regardless of the expertise of the personnel interrogating an implant, including in the most up to date CRMD clinic, no reliable hardware data is available except for the pulse generator or equivalent component.

It would be a great advantage and potentially lifesaving if the ER physician (or ambulance emergency medical technician) could very quickly identify, at a minimum, the type of pulse generator implant, manufacturer and model number. In certain cases, for example, with a pacemaker patient who is in cardiac distress, quickly identifying and obtaining the appropriate external programmer could allow the ER physician or other appropriate personnel to boost the pacemaker output voltage and/or pulse rate to properly recapture/stimulate the heart to contract at a programmed or other appropriate rate, thereby improving the cardiac output, and or other hemodynamic parameters. A variety of other programmable stabilizing adjustments may also be made as required. It should also be noted that, for the vast majority of AIMDs it is not possible to just change the battery when the battery is depleted. Because the AIMD housing has been laser welded and hermetically sealed, access to the battery is really not possible in an operating room theater. Accordingly, when the battery is depleted, it is typical that the entire device is replaced and the new pulse generator plugged into the existing lead system. All of the time lost while trying to identify the right programmer can be detrimental not only to the patient, but also detract attention from other critical tasks for that patient and for other patients in the ER. Accordingly, there is a need for a way to rapidly identify the type and model number of an AIMD so that it can be rapidly identified and/or other appropriate activities initiated.

It is also important to note that the lead systems of pulse generators or other AIMDs generally remain in the human body much longer than the AIMD itself. For example, in the case of a cardiac pacemaker, the pulse generator power cell (battery) may last for three, five or even over 10 years depending on a variety of programmed settings and other features, whereas leads (the insulated conductors connecting the pulse generators to the heart) should have a very low failure rate even after 10 years in the human body. Changing the pulse generator is, from a technical perspective, a relatively minor procedure whereas the removal of leads from the heart, once they have been implanted for greater than 6 months to a year, requires relatively sophisticated equipment and surgical skill and is considerably more risky for the patient. This is because the lead insulation tends to become embedded and overgrown by scar tissue. This can involve the whole length of the lead and tends to be particularly dense in the great veins, adjacent to a heart valve and adjacent to electrodes. Thus, on occasion even open heart surgery may be required to remove lead systems. In contrast, when a pacemaker is replaced, the tissue over the pulse generator is simply incised, the old pulse generator disconnected and the existing lead(s) plugged into the new pacemaker.

Unfortunately, it is not uncommon for leads to fail for various reasons and when this occurs, they are usually simply left in place in the body. They could fail due to breakdown of the insulation, fracture of the conductor, etc. Leads may also be abandoned because they have migrated to an improper position within the heart, etc. When a lead is abandoned, the physician normally snips off the connector(s) and attaches the remnant to the adjacent tissue. New leads are then implanted often in parallel with old abandoned leads.

Abandoned leads are often well tolerated, but there is extensive literature on the complications they can cause, including venous obstruction, infection, rhythmias, damage during MRI procedures, etc. For example, it has been demonstrated that during an MRI procedure, abandoned leads can significantly overheat due to the powerful RF and magnetic fields induced during MRI.

Accordingly, it is important that there be a way of identifying not only the presence of abandoned leads, but also the precise lead type and model. This applies not only during follow-up of complex patients (and they are common), but also when device patients are presented to an Emergency Room under various circumstances. Regardless of the circumstances under which a medical practitioner may contemplate performing a medical diagnostic procedure on the patient such as MRI, that patient, and in fact, all patients, will be well served by caregivers being able to rapidly and efficiently identify the make and model number of all IMDs, leads and other components like adapters, and all other implanted foreign materials whether functioning or abandoned. In addition, such technology should also improve the efficiency of product recall management.

It is important to note that certain lead systems are evolving to be compatible with specific types of medical diagnostic procedures. For example, US 2007-0112398 A1 and US 2006-0247684 A1, both of which are incorporated herein by reference, disclose the use of bandstop filters placed in series with leads or circuits of active medical devices to enhance their MRI compatibility. MRI systems vary in static field strength from 0.5 Tesla all the way to above 10 Tesla. A very popular MRI system, for example, operates at 3 Tesla and has a pulsed RF frequency of 128 MHz. There are specific certain lead systems that are evolving in the marketplace that would be compatible with only this type of MRI system. In other words, it would be dangerous for a patient with a lead designed for a 3 Tesla MRI system to be exposed to a 1.5 Tesla system. Thus, there is also a need to identify such lead systems and their associated AIMDs for medical personnel (such as the MRI technician or radiologist) when necessary, and to warn against potential highly dangerous therapeutic and diagnostic interventions.

Moreover, it would be beneficial if physicians were able to obtain additional information about an implanted medical device (IMD), lead system, and/or a patient. In addition to the manufacturer and model number of the device, such beneficial information could include the serial number of the device, the treating physician's name and contact information and, if authorized by the patient, the patient's name, contact information, medical condition and treatment, and other relevant information concerning device programmed parameters and the like.

However, although there are implanted medical devices which can be interrogated and read by communicators/programmers, typically the particular manufacturer's device must be used in order to interrogate and communicate with the implantable medical device (IMD). As indicated above, this can create many problems. Further, no currently available systems allow direct communication with leads and other non-pulse generator components to determine hardware details including date of and name of lead manufacturer, model number, serial number etc.

It has been demonstrated that RFID communicators, such as RFID readers, interrogators and emitters, can interfere with medical devices such as implanted cardiac pacemakers and implantable cardioverter defibrillators (ICDs). Initial studies conducted by the inventors have been corroborated through two extensive studies at the FDA Center for Devices and Radiological Health (FDA-CDRH). In laboratory studies in 2006 and 2008 at the FDA-CDRH, it was determined that RFID readers can and do cause potentially serious EMI to both cardiac pacemakers and ICDs. The FDA report entitled "In Vitro Tests Reveal Sample Radio Frequency Identification Readers Inducing Clinically Significant Electromagnetic Interference to Implantable Pacemakers and Implantable Cardioverter Defibrillators" was published in The Heart Rhythm Society journal. The FDA, in its 2008 study, referenced an article published in the New England journal of Medicine on May 27, 1997. This was a seminal paper authored by Dr. David Hayes, et al. where the possible types of responses to EMI of both pacemakers and ICDs were analyzed and classified. The paper classified the EMI responses into Type 1, Type 2 or Type 3 response. Type 1 EMI responses were defined as those that could or would be highly clinically significant including life-threatening responses. Other types of responses, which could simply be annoying, were categorized as Type 2, and others, Type 3, are really of no relevant clinical significance. An example of a Type 3 response would be when a pacemaker detects that EMI is present and goes into a fixed rate safety pacing mode (also known as noise reversion). This is not particularly desirable, but it is also usually not harmful to the patient for short periods of time. However, a Type 1 response would include, for example, prolonged pacemaker inhibition. This would mean that the pacemaker stopped delivering its life-giving output pulses. This could very quickly be life-threatening for a pacemaker-dependent patient.

Almost all modern pacemakers and ICDs incorporate feedthrough capacitor EMI filters to protect them against high frequency emitters, such as cellular telephones, microwave ovens and the like. U.S. Pat. Nos. 5,333,095; 4,424,551; and 6,765,779 illustrate and describe examples of such prior art feedthrough capacitor EMI filters.

FIG. 2 illustrates a prior art unipolar hermetic terminal 20 typically used in active implantable medical devices. Hermetic terminals typically consist of an alumina insulator 22 which is gold brazed 24 to a ferrule 26. In turn, the ferrule is typically laser welded 28 to the titanium housing 30 of an active implantable medical device. There is also a hermetic seal 32 that is formed between the alumina insulator 22 and the lead 34. This is typically also done by gold brazing, glass sealing or the like. There is also a prior art ceramic feedthrough capacitor 36 shown co-bonded to the hermetic terminal subassembly. Such feedthrough capacitors 36 are well known in the art for decoupling and shielding against undesirable electromagnetic interference (EMI) signals, such as those produced by cellular telephones, microwave ovens and the like. See, for example, U.S. Pat. Nos. 4,424,551; 5,333,095; 5,905,627; 6,275,369; 6,566,978 and 6,765,779.

FIG. 3 is a partial cutaway view showing the details of the prior art feedthrough capacitor 36 of FIG. 2. One can see that it has internally embedded electrode plate sets 38 and 40. Electrode plate set 40 is known as the ground electrode plate set and is coupled to the capacitor's outside diameter metallization 42. The active electrode plate set 38 is electrically connected to the capacitor inside diameter metallization 44.

FIG. 4 is a schematic diagram of the prior art feedthrough capacitor 36 illustrated in FIGS. 2 and 3. Prior art feedthrough capacitor EMI filters are generally of relatively low capacitance value (generally below 10,000 picofarads). As shown in schematic of FIG. 4, it forms what is known in the art as a single element low pass filter.

Due to size and other limitations, the capacitance value of these prior art low pass feedthrough capacitors is relatively low in value. Because of its low capacitance value, the filter is not effective at attenuating low frequencies, such as for LF RFID readers. In fact, in the LF reader frequency band of 125 to 135 kHz, prior art feedthrough capacitor filters provide less than 0.5 dB of attenuation. These prior art filters are particularly effective, however, for UHF readers operating at 915 MHz. In these bands, the AIMD filter provides well over 30 dB of attenuation and in many cases, above 50 dB.

The results from the FDA RFID reader studies of pacemakers and ICDs exactly correlate with this. There were no Type 1 responses for any UHF reader operating at 915 MHz. However, for LF and HF readers, the FDA documented a high number of life-threatening Type 1 responses out to a distance of 60 cm.

FIG. 5 is a family of curves which illustrates the performance of the prior art feedthrough capacitors illustrated in FIGS. 2, 3 and 4. In FIG. 5, one can see that the attenuation in decibels (dB) varies with frequency. These are also known in the art as single element low pass filters. In prior art pacemakers and implantable defibrillators, the inventors have found that the value of the feedthrough capacitor, which is intended to provide protection to EMI from cellular telephones, generally varies from 400 picofarads up to about 4400 picofarads (a very few designs go as high as 10,000 picofarads). One can see in FIG. 5 that at 915 MHz, all of the feedthrough capacitor values offer substantial attenuation (above 30 dB). This is why in the FDA studies, no clinically significant Type 1 EMI responses to pacemakers and ICDs at the 915 MHz RFID frequency were found. However, when one examines the 13.56 MHz frequency, one will see that high value feedthrough capacitors (in the range of 2700 to 4400 picofarads) offer a substantial amount of attenuation which varies from 17 dB to approximately 23 dB. However, some pacemaker/ICD manufacturers use relatively low value feedthrough filters in the 400 to 1200 picofarad range. In general, those do not offer sufficient attenuation at 13.56 MHz. This is why some manufacturers of pacemakers and ICDs exhibited no problems during the FDA HF testing (no Type 1 responses) whereas other pacemakers did show Type 1 responses. It should also be noted that on FIG. 5, LF (125 to 135 kHz) is substantially to the left (not shown) on the frequency axis. In FIG. 5, the frequency axis starts at 1 MHz and goes up to 915 MHz. For LF, no matter what the value of the feedthrough capacitor (from 400 to 10,000 picofarads) the attenuation is less than 0.5 dB. In other words, prior art feedthrough capacitors are totally ineffective at LF RFID frequencies and there is virtually no passive filter protection at LF frequencies at all for pacemakers and ICDs.

Passive filters include capacitors, inductors and resistors. The word "passive" means that, unlike electronic active filters, passive filters do not require a power source. Passive filters are preferred for EMI low pass filters because they can handle very high amplitude signals (like EMI from cellular phones or RFID readers) without becoming non-linear. Active filters can be designed to operate at LF frequencies. However, since they are based on very low voltage micro electronic circuit chips, they have a very limited dynamic range. It has been demonstrated that active filters become very non-linear and ineffective in the presence of high amplitude signals such as those produced by cellular phones or RFID readers. Accordingly, the AIMD manufacturer really does not have any practical design options to provide effective EMI filtering at LF RFID reader frequencies. Active filters become non-linear in the presence of high intensity RFID fields which rule them out. For an implanted passive filter to be effective at LF, it would need to be several orders of magnitude higher in capacitance value compared to prior art feedthrough capacitor filters. This would make it much too large in both volume and weight (the passive filters would almost be the size of a modern pacemaker). Worse yet, such passive filtering would degrade the essential performance of a pacemaker or ICD sensing circuits (pulse degradation, ability to sense biologic signals, etc.).

FIG. 6 illustrates typical (text book) sensing curves for both pacemakers and ICDs. The approximate center of these curves, where the devices are the most sensitive, is around 10 to 100 Hz. This means that signals that fall within this passband are meant to be sensed by the cardio rhythm management device (CRMD). In the case of an ICD, this would be down in amplitude as low as approximately 100 micro-volts and for a pacemaker approximately 0.8 millivolts. This is a range of biologic energies that are produced by the human heart. It is important that the pulse generator sense these energy levels so that it can inhibit (not compete) in the presence of a proper heart beat (proper sinus rhythm) or trigger off of an atrial rhythm in a patient with complete heart block; and so that an ICD can deliver high energy shocks in the presence of ventricular fibrillation. Delivering only essential stimuli is an important battery saving feature as there is no reason for the PG to supply electrical stimuli if the patient has their own "normal" sinus rhythm.

It is instructive to look at FIG. 6 and reflect on what happened a number of years ago when there were numerous reports of cellular telephones interfering with cardiac pacemakers and ICDs. Obviously a cellular telephone transmits at much higher frequency than those illustrated in the sensing curves shown in FIG. 6. However, what happens is that a high frequency carrier, such as that of a cellular telephone which is around 1000 MHz, would enter into previously unfiltered pacemakers and encounter a nonlinear circuit element such as a protection diode. These nonlinear circuit elements act as a demodulator. One of the worst offenders was the old TDMA 11 Hz modulated cellular telephone. Even though it operated at very high frequency, the nonlinear diode elements of a pacemaker would demodulate or strip off the 11 Hz modulation signal, which would fit right into the sensitive portion of the pacemaker passband of FIG. 6 and be over-sensed. Oversensing means that the pacemaker would incorrectly interpret this 11 Hz EMI modulation as a normal cardiac heartbeat and inhibit. This is particularly life-threatening for a pacemaker-dependent patient whose every heart beat depends on a proper pulse from the pacemaker. Having the pacemaker stop working or inhibit in this situation is immediately life-threatening. Having an antitachycardia device interpreting the EMI as a high risk ventricular rhythm can be equally confusing and dangerous.

With this understanding, one can now look at the table of FIG. 7. It is extremely unfortunate that the RFID industry has chosen modulation frequencies that fall generally in the range that would fit into the most sensitive portions of both the ICD and pacemaker passband sensing curves. For example, referring to FIG. 7, one sees listed here thirteen different types of RFID readers that were recently tested by the FDA shown in the left hand column. For example, RFID Equipment Code 2 operates at 134 kHz (0.134 MHz), but has a modulation of 14.43 Hz. It was predicted by the members of the Association for the Advancement of Medical Instrumentation Pacemaker Electromagnetic Interference Task Force PC69, that this was likely to be a problem. In fact, in the FDA laboratory tests, all of the LF and many of the HF RFID readers that had pulse repetition rates within the pacemaker passbands indeed caused pacemaker inhibition and/or other types of highly clinically significant Type 1 life-threatening responses. It is also interesting to note, referring to FIG. 7, that the readers that are marked CW (continuous wave) have no modulation content. These CW readers exhibited no Type 1, 2 or 3 responses to pacemakers or ICDs. One might be tempted to immediately jump to the conclusion that a simple way around this entire problem would be to simply restrict the RFID industry to only use CW readers. The problem with that is that CW readers, by definition, can only activate a tag and detect the presence of a tag and can obtain only very limited information. In other words, they can't really transmit back and forth (read/write) any detailed useful information. Accordingly, use of CW tags and readers will not allow for full identification of model number, serial number, and patient information related to an AIMD.

The FDA has conducted two extensive trials testing both pacemakers and ICDs in a laboratory environment wherein cardiac pacemakers and implantable cardioverter defibrillators (ICDs) and their associated leads were placed into human phantom saline tanks and exposed to various model RFID readers and associated systems. FIG. 8 summarizes the testing that was performed by the FDA-CDRH in 2006 and 2008. There were a total of 37 pacemakers and 34 ICDs tested. A total of 20 RFID systems were also evaluated. This testing was blinded in that the results were given letter codes so that no one reading the reports could tell who was the manufacturer of the particular pacemaker or who was the manufacturer of the particular RFID system. It should be noted that all the major pacemaker and ICD manufacturers in the world participated in this testing by providing their devices.

FIG. 9 is a top down view of a grid placed over the saline tank used for this testing at the FDA. In 2006, a spiral lead configuration was used in accordance with ANSI/AAMI Standard PC69. In 2008, a more representational human implant geometry was used based on the distances of the lead bodies and electrodes from the pulse generator observed on patient X-rays.

FIG. 10 shows a similar set up for ICDs. On the right hand figure (2008), one can see a loop L representative of where excess leadwire would be wound up either in or adjacent to a left pectoral ICD pocket. The configuration is typical for leads passing from the left pectoral region to terminate in the right ventricle and right atrium.

FIG. 11 is a cross-section of the human phantom saline tank showing the implant (pacemaker or ICD) just below (0.5 cm) the surface of the fluid. It has been shown in the past that this type of model very accurately represents the fields that will occur inside the human body. Saline solution of 500 ohm-cm is used in the tank, which replicates the dielectric properties of body fluids. Thus, such a saline tank closely replicates the EMI characteristics encountered by a device that has been implanted inside the human body. The testing, as performed by the FDA, was done with the antenna suspended in a robotic arm that could carefully step the RFID antenna away in discrete distances so that accurate threshold distances for Type 1, 2 and 3 responses could be recorded.

The following definitions are provided to assist with a better understanding of the ratings applied to the FDA electrocardiogram (EKG) tracings in FIGS. 12 through 20. Class 1 responses include transient ventricular inhibition for 3 seconds or more, persistent ventricular inhibition or any change in pulse generator programmed settings. It should be noted that throughout all of the RFID testing, to be discussed in more detail below, there was never a change in programmed settings. In other words, when the RFID reader was removed or turned off, the EMI response immediately ceased. Class 2 responses are defined as transient (intermittent) ventricular inhibition for more than 2 seconds, but less than 3 seconds. Class 2 responses also include transient, continuous atrial inhibition or rate adaptive pacing. Class 2 responses are not considered to be immediately life-threatening, but are considered to be very undesirable. For example, persistent very high rate stimulation of the heart can produce irreversible damage and/or death, particularly in heart failure patients, patients with ischemic heart disease and others. Class 3 responses are defined as any other type of interference which includes transient inhibition of less than 2 seconds, and/or noise reversion mode pacing. This is a software circuit feature where the pacemaker detects EMI and reverts to a non-responsive fixed rate (metronome like) stimulation. This is similar to what occurs after a magnet is applied over a pacemaker to close a reed switch, for example, to bypass the circuit that ordinarily decides whether pacing is required or not based on the feedback electrical signals that are being received from the heart. Class 3 responses are undesirable but not considered to be clinically significant.

FIG. 12 shows an EKG baseline strip of a pacemaker in the saline tank without an RFID reader present. Normal pacing pulses are shown with the atrial pulses A shown on top and the ventricular pulses V shown on the bottom. One can see that every time there is an atrial pulse, a ventricular pulse follows after the programmed delay (PD). This A-V delay is a normal function as it also occurs naturally during sinus rhythm within the human body. Also notice that the atrial pulses are all equally spaced as are the ventricular pulses. This is what would be observed when a pacemaker is functioning normally.

FIG. 13 is the same EKG strip as FIG. 12 except in this case an RFID reader has been brought close to the pacemaker and/or its leads in the saline test tank. High frequency (HF) electrical activity is present on the baseline. Although not in any way similar to a physiological signal, in this case, the pacemaker has incorrectly over-sensed and interpreted the RFID signal as a normal heart rhythm and has completely shut off (inhibited) pacing output (atrial and ventricular inhibition). If the patient in whom the pacing device had been implanted had no intrinsic heart electrical rhythm all of the time (was totally pacemaker dependent), or just some of the time (was partially or intermittently pacemaker dependent), the inhibition shown in FIG. 13 either would or could be immediately life-threatening, respectively. Very early on in one of the inventor's experience as a physician with demand pacemakers, this resulted in the death of a very intermittently dependent patient farmer when he was driving his tractor just as he had done many times previously without difficulty. Several identical model demand pacemakers from the same company were then tested while in the shirt pocket of someone sitting in the driver seat of the same model tractor. Inhibition was 100% in all cases caused by EMI from the tractor motor ignition system. It is important to emphasize that intermittent pacemaker dependency (and potentially dependency on other life supporting devices) is common and by its very nature, is under-reported based on the parallel intermittency of follow-up clinic visits. Even if the patient usually has an intrinsic rhythm, dependency for just a few minutes during an overlapping period of exposure to EMI will be fatal. Similarly, patients' lives and well being are frequently at risk because of lack of availability of accurate medical device and clinical data.

FIG. 14 is a pacemaker EKG strip which illustrates another type of Class 1 response involving continual or prolonged ventricular inhibition with individual episodes lasting longer than 3 seconds. As one can see, there is a ventricular stimulus (V1) at approximately 135.5 seconds and then another ventricular stimulus (V2) at 142.2 seconds. Atrial stimulus pulses are shown as A1 through A7 and are undesirably irregular (however, transient atrial inhibition is not considered life-threatening). Any transient ventricular inhibition that lasts 3 seconds or more is considered a Class 1 or potentially life-threatening response.

FIG. 15 is an EKG tracing which shows high frequency RFID EMI (HF EMI) on the baseline tracing, which an ICD has incorrectly interpreted as ventricular fibrillation and delivered a high voltage shock (HV) after 53.4 seconds (if programmed on pacing was totally inhibited). This is defined as a Class 1 response because undesirable high voltage shocks are not only very painful for the patient, but can also result in serious accidents (an inappropriate ICD shock can knock a patient right off his feet and in one recent report actually induced ventricular fibrillation that the ICD could then not correct, i.e. was fatal).

FIG. 16 is a pacemaker EKG strip example of a Hayes et al. Class 2 inhibition showing occasional atrial and ventricular output suppression. This is a Class 2 response because of lack of complete atrial inhibition and because the ventricular pulse inhibition is frequently at least two seconds, but for less than three seconds in duration. It should be noted that no Class 2 responses were found in any of the FDA testing (all responses recorded in the 2008 FDA study were either Class 1 or Class 3).

FIG. 17 is a pacemaker EKG strip of a typical Class 3 response. Through most of this EKG strip, one can see normal atrial (A) and ventricular (V) stimuli. However, at the 49 second point, there is an approximately 33% lengthening of the A-A (A1-A2) interval similar to what is seen with occasional T-wave over-sensing at the atrial electrode. This is of no clinical significance and many patients are unaware of a transient slowing of the stimulation rate.

FIG. 18 is a pacemaker EKG strip example of occasional atrial output stimulus inhibition (A) associated with what is most likely atrial triggered ventricular pacing (V). This would be expected with selective detection of EMI on the more sensitive atrial channel versus the less sensitive ventricular sensing circuitry. Atrial sensitivities are almost always adjusted to a low millivolt setting versus the ventricular sensitivities as the electrical signal associated with ventricular contraction is generally 4 times or greater than the discharge associated with contraction of the relatively thin atrial wall muscle. Regardless, intermittent loss of atrial ventricular synchrony would rarely be life-threatening for the patient even if it persisted for a long period of time.

FIG. 19 is an EKG strip example of the injection of a CENELEC wave signal, intended to stimulate a normal biologic cardiac electrical signal, into the saline test tank. In engineering terms, the CENELEC signal is intended to represent normal heart electrical activity although the 11 Hz (660 PPM) frequency seen on the baseline is more representative of poorly organized atrial or ventricular fibrillation. It is expected that a normally operating pacemaker will be completely inhibited. In other words, what FIG. 19 should look like is the EMI tracing in FIG. 13. The object of complete pacing output inhibition during normal heart rhythms is to avoid delivery of even occasional unnecessary ventricular stimuli (V), as these could result in competition between paced and intrinsic heart action in a patient. This type of interaction is also considered of minor Class 3 clinical significance.

FIG. 20 is an EKG strip example of a pacemaker apparently not responding properly to the CENELEC injection signal, the presence of which is clearly documented on the baseline. The expectation was that the delivery of stimuli by the pacemaker would be completely inhibited as shown in FIG. 13, but in this case as a normal response to a satisfactory patient-generated heart rhythm. Instead, when the RFID reader was brought close to the pulse generator, the sensing circuit responded to the reader EMI and or classified the supposedly physiologic signal as EMI and automatically switched into the noise reversion (fixed rate) pacing mode, previously outlined as part of the Hayes et al. Type 3 definition. Thus the pulse generator continued to deliver A-V sequential stimuli at regular intervals similar to what was illustrated in FIG. 12, but because of the sensing circuits being bypassed, the atrial (A) and ventricular (V) stimuli in FIG. 20, would be competitive with a patient's underlying heart rhythm. By competitive, we mean the stimuli would fall randomly onto various portions of the intrinsic cardiac action. This is not particularly desirable because while infrequent, application of electrical stimuli while the cardiac tissues are repolarizing (recharging following a muscular contraction) can be arrhythmiagenic. However, this is considered a lesser risk than allowing the pacing circuits to be shut off by EMI, because all patients are potentially dependent at one time or another.

FIG. 21 is a bar graph summarizing the FDA 2006 and 2008 pacemaker test data at LF, HF and UHF RFID frequencies. Unfortunately, in 2006, pulse generator responses to the testing were not identified as clinical Type 1, 2 or 3. In other words, trivial and potentially life-threatening responses were lumped together. For example, for 134 KHz (LF) in 2006, 83% of pacemakers tested showed an EMI response. However, the 2008 test stratified the LF data to reveal that 46% of the pacemakers had a Type 1 (life-threatening) response, whereas 32% had a Type 3 response and 22% of the devices were entirely unaffected (these were all unmodulated CW readers). Note: there were no Type 2 responses. A similar range of responses and effects were noted during the testing of the 13.56 MHz (HF) readers. In 2006, a total of 18% of units were affected by the EMI, whereas in 2008, this was refined to show that 7% of devices had a Type 1 response and 4% had a Type 3 response. In 2006, at UHF frequencies, 6% had a response, but this represents only a single pulse generator. It was later determined that this particular pacemaker model did not have a feedthrough capacitor filter. This situation was since rectified through manufacturer re-design. Accordingly, in 2008, none of the pulse generators were affected by any of the readers transmitting 915 MHz signals.

FIG. 22 is a bar graph summarizing the FDA test data that is very similar to FIG. 21 except it's for ICDs. It should be noted that 55% of ICDs tested in 2008 at LF showed a Class 1 response. This is unfortunate because 134 kHz is an ideal frequency for continuous reader signal emissions to decode a tag embedded deeply inside of body tissue, within the header block, or even inside the housing of an active implantable medical device.

FIG. 23 is a comparison of all of the different types of LF readers tested by the FDA. The reader numbers 1, 2, 3, 4 and 5 correlate with the same RFID equipment code numbers previously described in FIG. 7. As one can see, for RFID reader #1, which was CW, there was no deleterious effect on any of the pacemakers tested. Reader #3, which has a modulation of 11 Hz, affected the greatest number of pulse generators (61% Class 1 and 31% Class 3). This is not particularly surprising if one refers to FIG. 6 and sees that the most sensitive part of both the pacemaker and ICD sensing curves occur at about 11 Hz. The main take-away or summary from FIG. 23 is that all of the modulated low frequency (LF) readers have the potential to cause dangerous pulse generator responses (Class 1) in essentially every patient. As previously explained, pacemakers and ICDs really have no practical defense (EMI Filter) to an LF signal that contains modulation within their passband.

FIG. 24 is a bar graph very similar to FIG. 23 except that it compares LF reader FDA test results for ICDs. Again, use of CW reader #1 had no ill effects. However, with reader #3, which has a modulation of 10.5 Hz (which falls right into the ICD sensing passband of FIG. 6), 81% of all responses were Type 1, that is, associated with high clinical risk.

FIG. 25 is a bar graph which is very similar to FIGS. 23 and 24. However, this is a comparison of pacemaker responses at the 13.56 MHz (HF) RFID carrier frequency. Again, reader #8, which is CW, had no effect on any of the pulse generators tested. However, readers #6 and #10 both with 11 Hz modulation resulted in the most detrimental pulse generator responses (13% Type 1 in both cases).

FIG. 26 is a bar graph which illustrates FDA tests using the same HF readers and carrier frequencies as FIG. 25, but for ICDs. Under these test conditions, ICDs tend to be much less susceptible to adverse reader effects than pacemakers. This is likely due to the fact that ICDs are slower to react in providing a high voltage shock as it takes time to charge their high energy internal capacitor, and before pulse delivery a re-interrogation takes place to make sure the dangerous tachyarrhymia is still present.

FIG. 27 summarizes the threshold distances for EMI responses in the FDA RFID reader testing. The greatest distance at which any response was documented was out to 60 cm. This is of great concern compared to the original cell phone work where it was determined that maintaining a transmitter to pulse generator separation greater than 15 cm would be safe. For Type 1 life-threatening responses, the greatest distances that could lead to an adverse effect was 40 cm with LF readers, and 20 cm for HF readers. For ICDs, the reactions tended to require closer proximity. For any response, the threshold distance was 40 cm. For a Type 1 response, the RFID reader had to be held within 12.5 cm of the implant in the saline tank. In no case were there any Type 1 responses for UHF readers. All of these recorded threshold distances are of particular concern for an RFID reader that is designed to directly interrogate an AIMD such as a pacemaker or ICD (to determine the model number, type, serial number, etc. of the implanted device). In these cases, for example in an ambulance or emergency room, the RFID reader would be held as close as 2 cm to the implanted device. The potential for a life-threatening Class 1 response is evident.

Similar concerns are present with other types of LF and HF reader applications which a pacemaker or other AMD/AIMD patient may encounter in the patient's normal environment. For example, keyless entry systems for automobiles generally operate at LF frequencies. The car itself transmits an LF RFID signal which detects the driver/passenger/patient walking up to the automobile where the automobile goes into an active (pinging) mode generating a powerful LF frequency to detect the approach of the driver or passenger who may also possibly be an AIMD patient. When the person nears the car with the car's RFID tag either in his pocket, associated with a wrist watch or other type of container (like a purse or wallet), the car door will automatically unlock (open). Some new automobiles also incorporate a back-up RFID reader system in the driver's seat. For example, in some models, an RFID antenna is also embedded within the driver's side seat back wherein the car tag is reinterrogated to make sure the correct person is inside the car before the ignition will start (this is an anti-high jacking feature). Of course, all of this is of great concern if the particular driver happens to be a pacemaker or ICD patient. Of particular concern however, would be the unmodified inclusion of a LF RFID transmitter in the wand head of a CRMD programmer, which by design would be brought into close proximity to large numbers of implanted heart rhythm control devices.

Accordingly, there is a need for an RFID-enabled external AIMD telemetry programmer which incorporates built-in safeguards for protecting sensitive AIMD device electronics against RFID-associated electromagnetic interference (EMI). More particularly, an RFID-enabled external AIMD telemetry programmer system is needed for rapidly identifying information about the implanted medical device and/or information about the patient while at the same time, protecting the AMID against RFID-associated EMI. Such systems must be able to identify active and passive medical devices through use of RFID technology without causing the AMD or PMD to malfunction. The present invention fulfills these needs and provides other related advantages.

SUMMARY OF THE INVENTION

The present invention is directed to RFID-enabled external AIMD telemetry programmers. Most hospital emergency rooms worldwide have at least one of these programmers to handle situations of cardiac emergency. In the present invention, a prior art telemetry external programmer is modified such that an RFID reader is integrated into the external AIMD telemetry programmer, connected to it, or plugged into one of its many ports, or preferably included in the standard programming wand head. For example, in one embodiment, a USB port is used to interface with a tethered reader or reader antenna. The reader could be read only or it could be read/write. With the read/write type device, it would be possible to reprogram an RFID tag that was already implanted within a patient's body. The RFID tag can be disposed anywhere within the patient, such as directly on or in the AIMD itself, or its associated leads, or anywhere else within the human body, for example, in the area of the patient's wrist.

The RFID reader or reader/writer may be designed into, connected to or attached to the external AIMD telemetry programmer. Software and possibly hardware modifications or upgrades are made to the external AIMD telemetry programmer and accessories to enable it to work with the added RFID circuitry. In a preferred embodiment, the AIMD external programmer is similar to a laptop computer wherein the software modifications enable its display and keyboard to be used during RFID interrogation and/or RFID tag patient and lead/threshold specific reprogramming/data entry (writing).

The present invention also resides in an RFID-enabled AIMD external programmer which incorporates special circuitry for protecting an AIMD electronic circuit against RFID-associated electromagnetic interference. The AIMD external programmer is enabled with a radio frequency identification (RFID) communicator which includes a circuit for limiting the total continuous transmit time of an electromagnetic signal. The communicator also includes a time-out circuit for delaying a subsequent transmission of the electromagnetic signal. The electromagnetic signal may comprise an RFID test signal, an RFID tag search signal, an RFID communication signal, an RFID interrogation signal, an RFID read signal, or an RFID write signal. The electromagnetic signal may be modulated or unmodulated.

The total continuous transmit time of the RFID electromagnetic signal is preferably no greater than five seconds. In a particularly preferred embodiment, the total continuous transmit time of the electromagnetic signal is five hundred milliseconds or less and the time-out circuit delays the subsequent transmission of the electromagnetic signal for two seconds or more.

The RFID communicator portion of the AIMD external programmer may comprise a read-only or a reader/writer device. The AIMD external programmer and its RFID communicator may be actively searching for or communicating with an RFID tag (even if no tag is present). The communicator may also be in communication with a computer or a computer network.

The RFID tag is associated with an object in close proximity to a patient having an active medical device, or is associated with the medical device, its leads, or abandoned leads, adapters etc. The RFID tag may also be located anywhere else within the patient, for example, in a patient's wrist. The RFID tag may comprise a read-only or a readable/writable RFID tag. Typically, the RFID tag comprises an antenna and an electronic micro-chip electrically connected to the antenna. The RFID tag may include retrievable information relating to the active medical device(s) and/or patient. The retrievable information may include information pertaining to MRI compatibility of the active medical device or an associated lead system. Initially tags will be passive but in the future, as implantable low energy generating systems become available, active tags may also come into use.

The active medical device may comprise any of the following: a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a carotid sinus stimulator, a bone growth stimulator, a gastric pacemaker, an endovascular catheter, a Bion or a prosthetic device, and component parts thereof, including lead wires and abandoned leads. The object in close proximity to the patient may comprise passive medical devices and components thereof, including any of the following: heart valves, stents, screws, plates, hip implants, knee implants, other prosthetics, braces, wristbands, necklaces, identification badges or cards, ankle bracelets, or eyeglasses.

The RFID-enabled AIMD external programmer may transmit an interrogation signal to the RFID tag when the communicator senses that the RFID tag is in close proximity. In such a case, the communicator will actively seek an associated RFID tag.

In actual practice, the RFID-enabled external AIMD programmer sends an RFID interrogation pulse and first determines what type of implanted device (e.g. pacemaker, ICD, defibrillator, drug pump, etc.) the device is. The programmer/communicator will also determine the manufacturer of the device, and the model and/or serial number of each tagged device present. The RFID tag may include physician information, patient information, etc. Such information may also include whether the device or lead wires are MRI compatible, and with which MRI RF pulse frequencies the device or lead wires are compatible.

The RFID communication system including the external AIMD programmer may also be in communication with a computer or a computer network. The RFID communicator or a connected computer network includes an electronic database with look-up tables enabling the communication between the communicator and the RFID tag. The electronic database or look-up table may reside in the computer or computer network, or in the communicator itself.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 2 is a fragmented sectional view of a prior art unipolar hermetic terminal typically used in active implantable medical devices.

FIG. 3 is an enlarged, partially fragmented perspective view of the feedthrough capacitor shown in FIG. 2.

FIG. 4 is a schematic electrical diagram of the coaxial feedthrough capacitor of FIG. 3.

FIG. 7 is a table showing all of the RFID readers that were tested in a 2008 battery of tests.

FIG. 8 is a summary of the testing that was performed by the FDA-CDRH in 2006 and 2008.

FIG. 27 is a summary of interaction distances.

DETAILED DESCRIPTION OF THE PREFERRED EMBODIMENTS

The present invention is directed to novel RFID communicators (readers/interrogators) that include a circuit for limiting the total continuous transmit time of an electromagnetic signal, and a time-out circuit for delaying a subsequent transmission of the electromagnetic signal. By limiting the total continuous transmit time of the electromagnetic signals, in the case of a cardiac pacemaker, only a few beats could be dropped, which is clinically insignificant to the patient. In other words, by limiting the transmit time and having a time-out period, the RFID communicator cannot transmit for a sufficiently long enough period to permanently harm the patient or cause a life-threatening arrhythmia. Hayes Type 1 (and even type 2) responses are rendered impossible.

Figure 1:
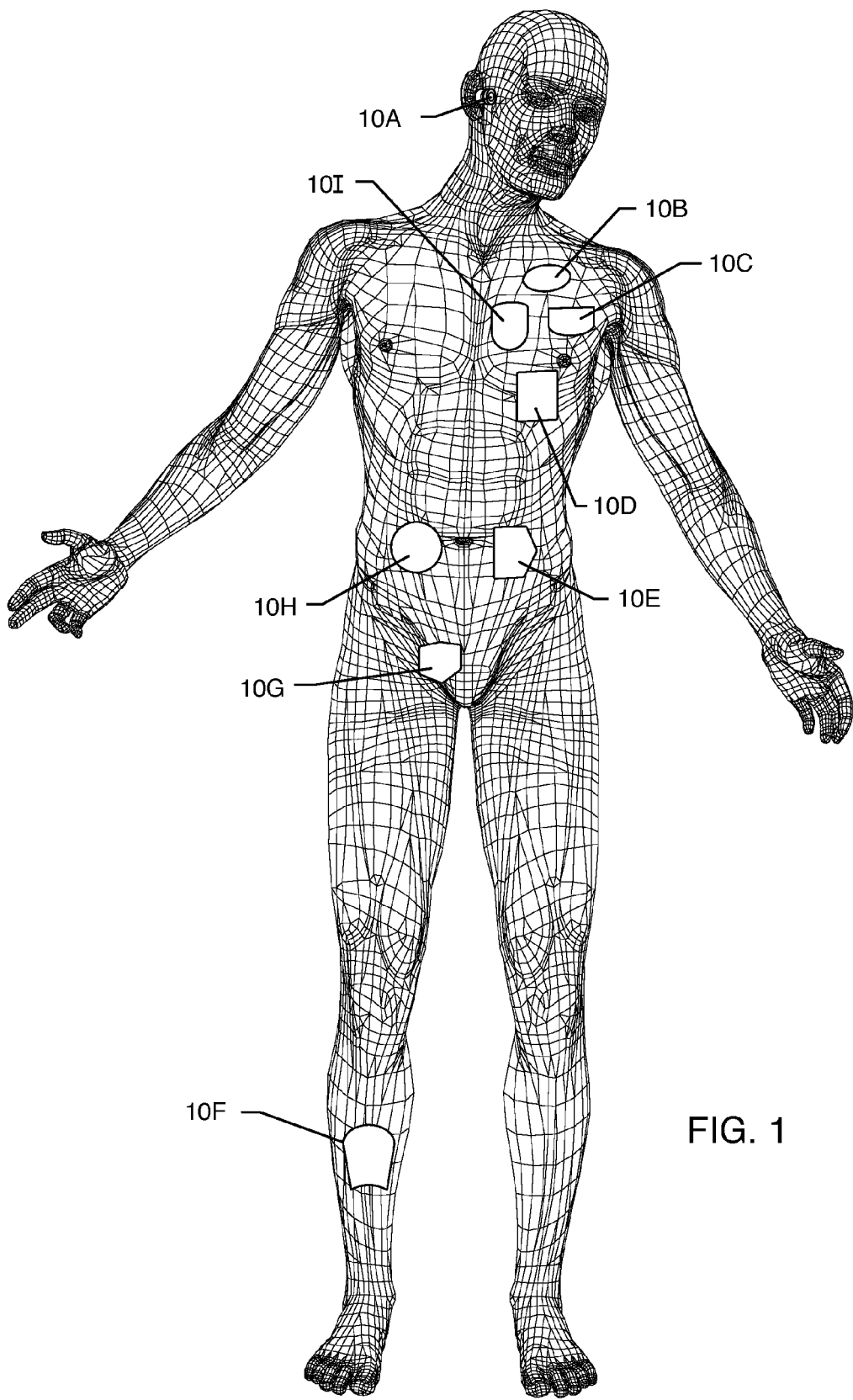
FIG. 1 is a wire-formed diagram of the generic human body showing a number of active and passive medical devices (AIMDs and PIMDs).
Figure 5:
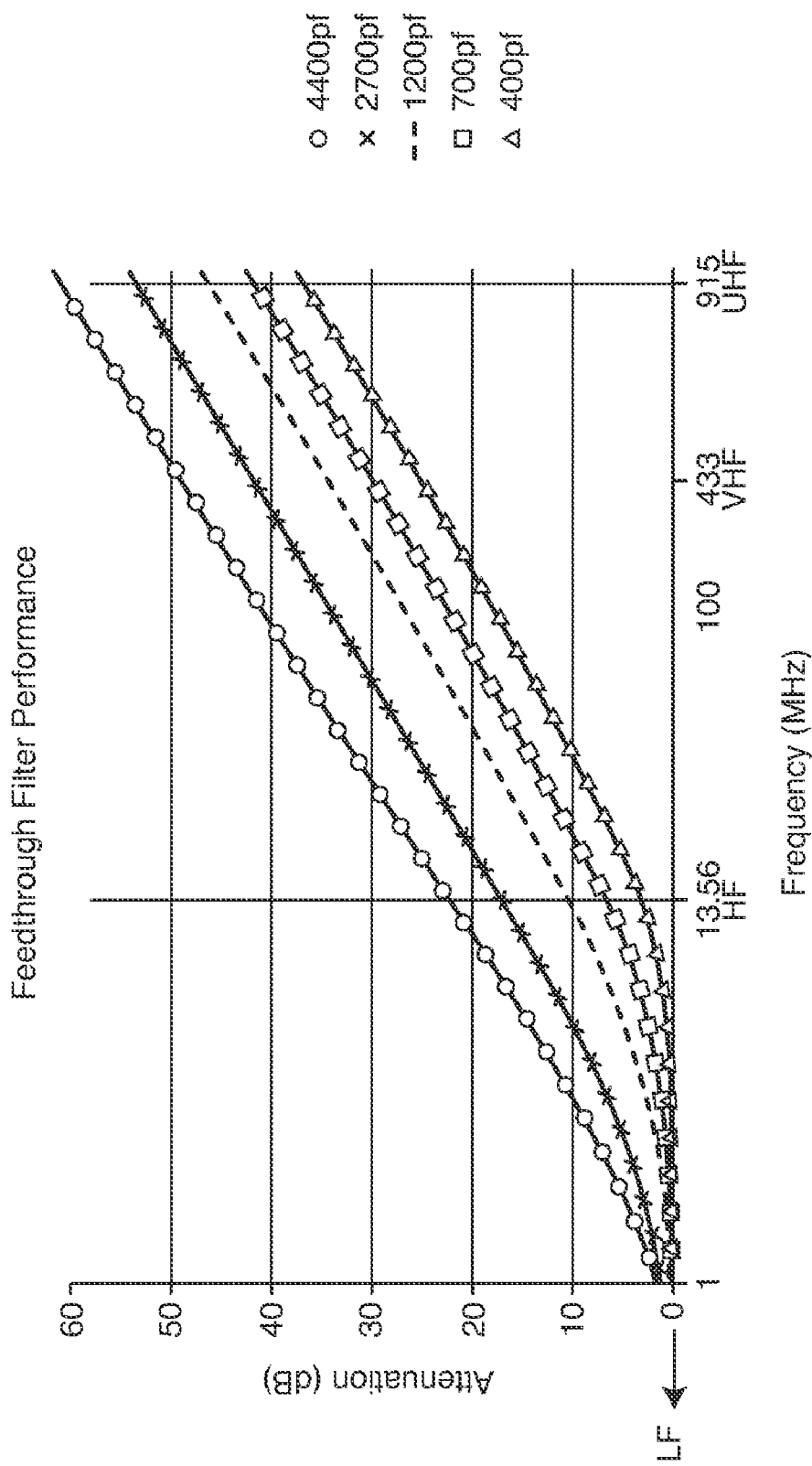
FIG. 5 is a graph illustrating the performance of four different feedthrough capacitors exposed to LF, HF, and UHF RFID signals.
Figure 6:
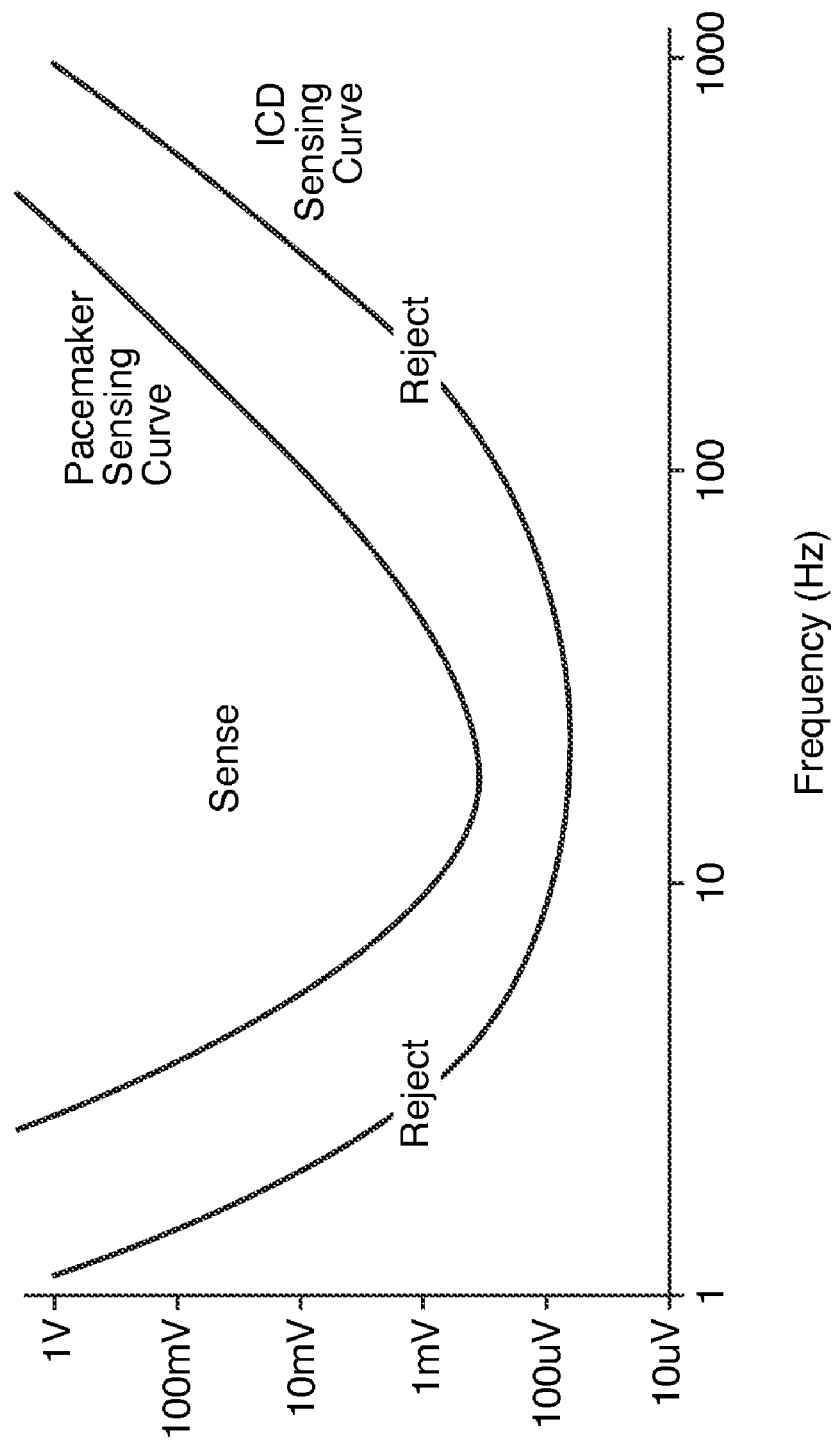
FIG. 6 illustrates a generic sensing curve for pacemakers and implantable cardioverter defibrillators.
Figure 9:
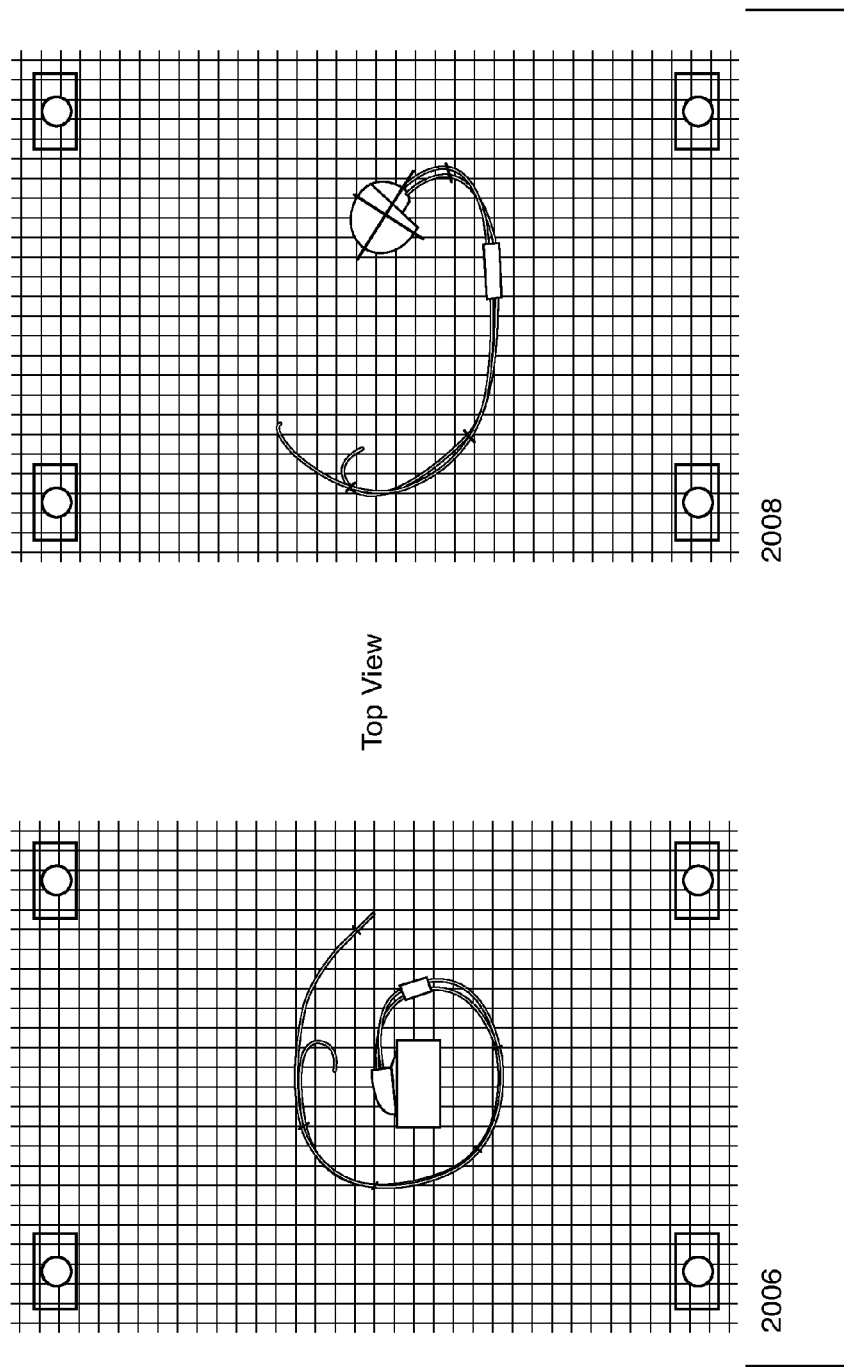
FIG. 9 is a plan view of a grid placed over the saline tank used for pacemaker testing by the FDA.
Figure 10:
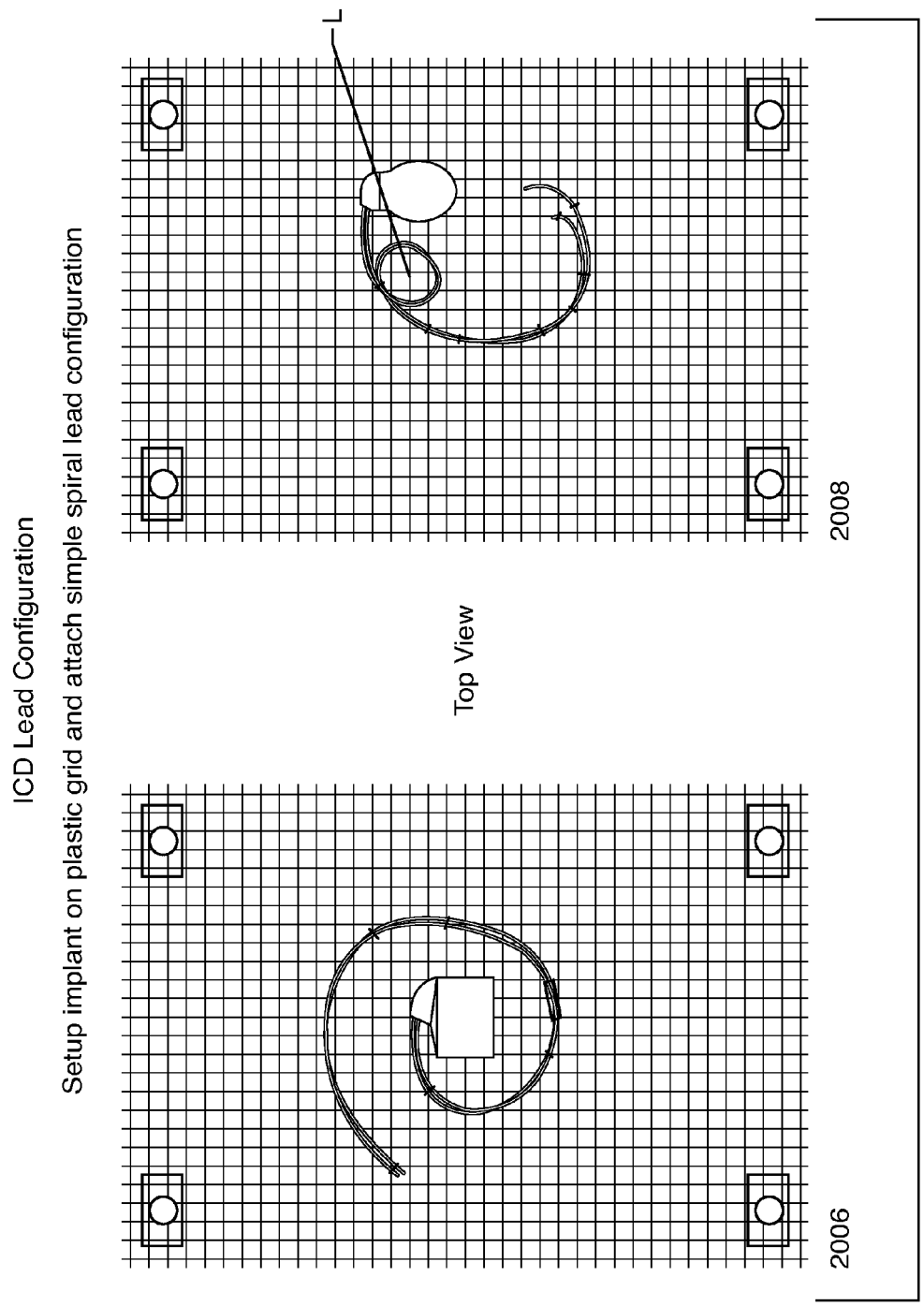
FIG. 10 is a plan view similar to FIG. 9 showing a similar setup for ICDs.
Figure 11:
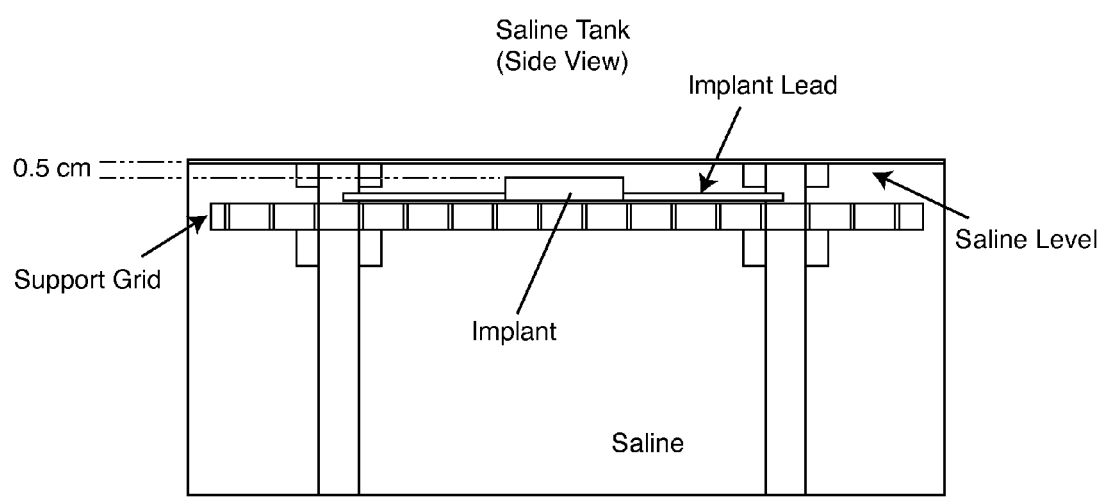
FIG. 11 is a cross-sectional view of the saline tank utilized in the testing mentioned, showing the implant just under the surface of the saline fluid.
Figure 12:
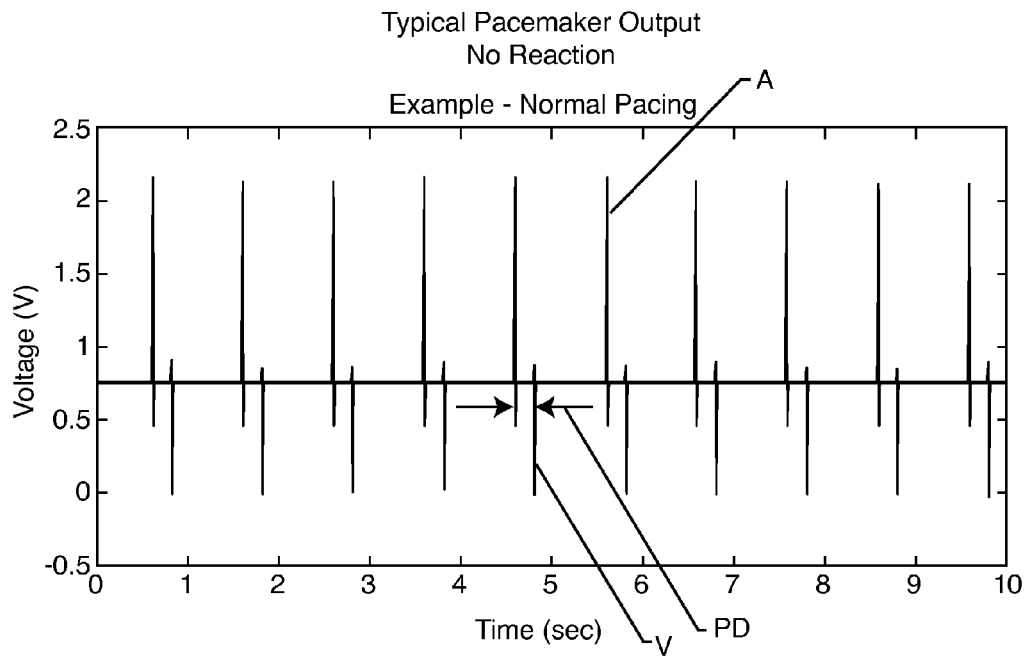
FIG. 12 shows a baseline of a pacemaker in a saline tank without an RFID reader present.
Figure 13:
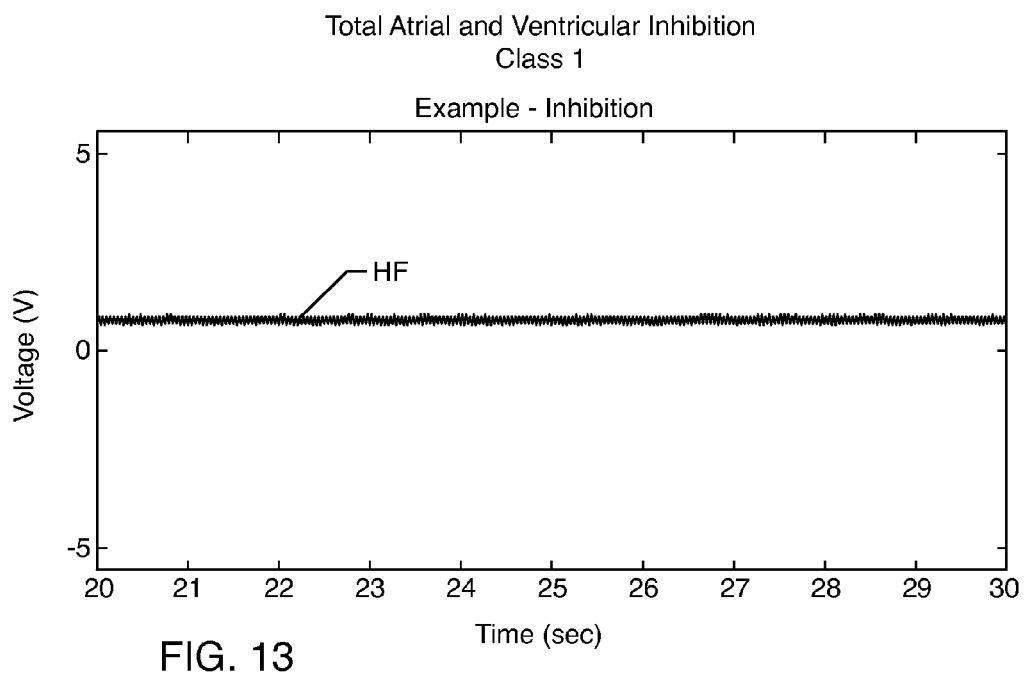
FIG. 13 is a graph similar to FIG. 12, except in this case an RFID reader has been brought close to the tank.
Figure 14:
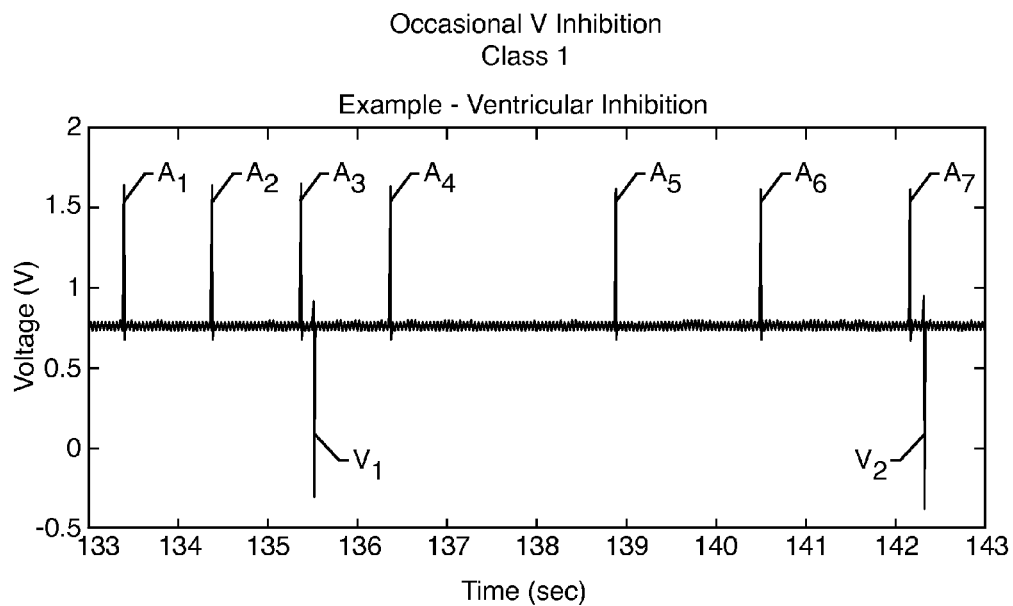
FIG. 14 illustrates a type of Class 1 response involving ventricular inhibition that lasts longer than three seconds.
Figure 15:
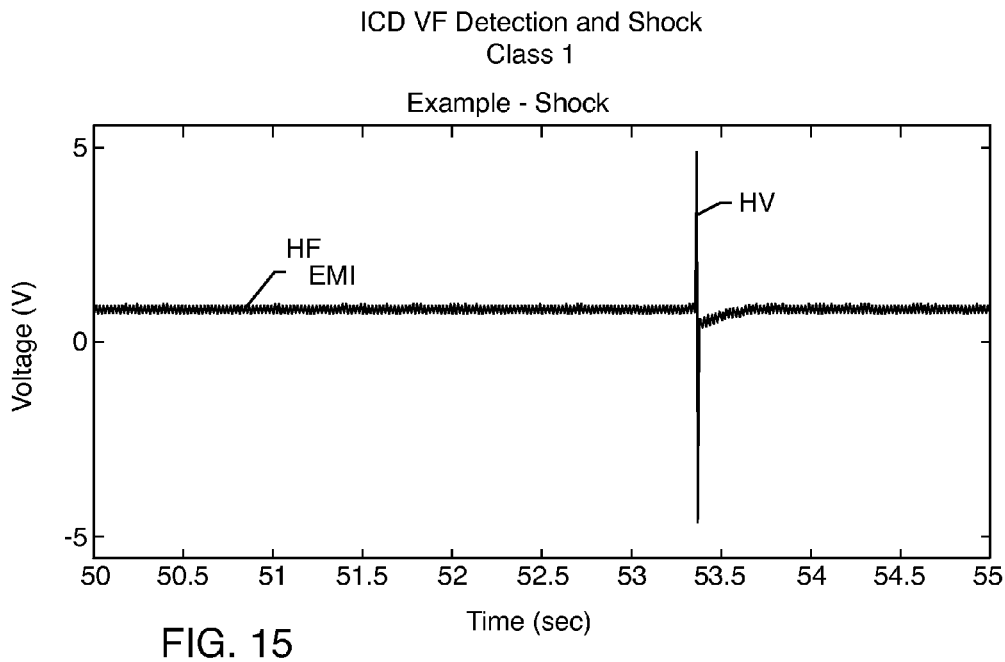
FIG. 15 illustrates the output detection on an ICD where a ventricular defibrillation was detected and a high-voltage shock was delivered if programmed pacing was totally inhibited.
Figure 16:
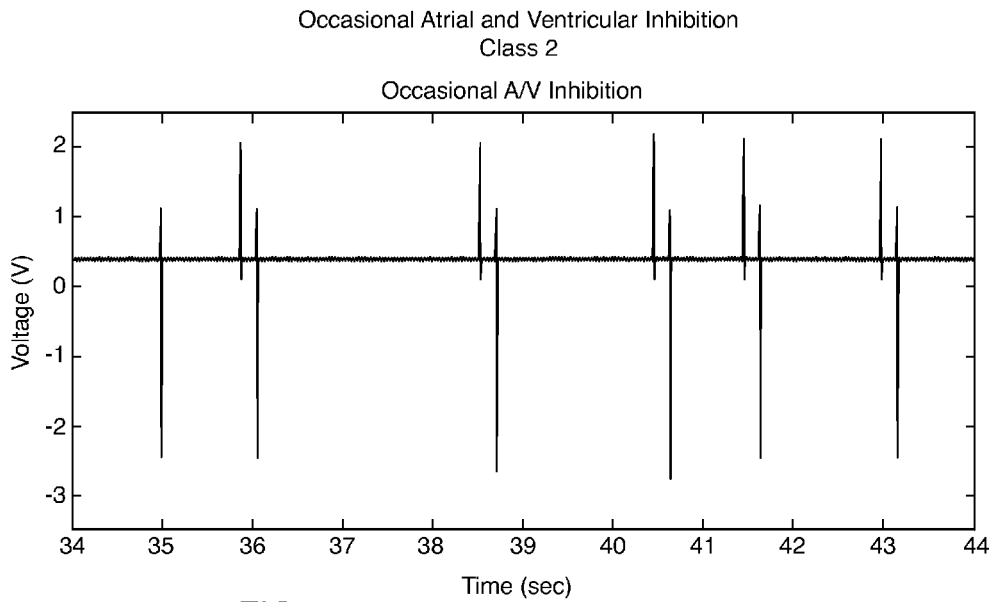
FIG. 16 is an example of a Class 2 response showing occasional atrial and ventricular inhibition at a maximum duration less than 3 seconds.
Figure 17:
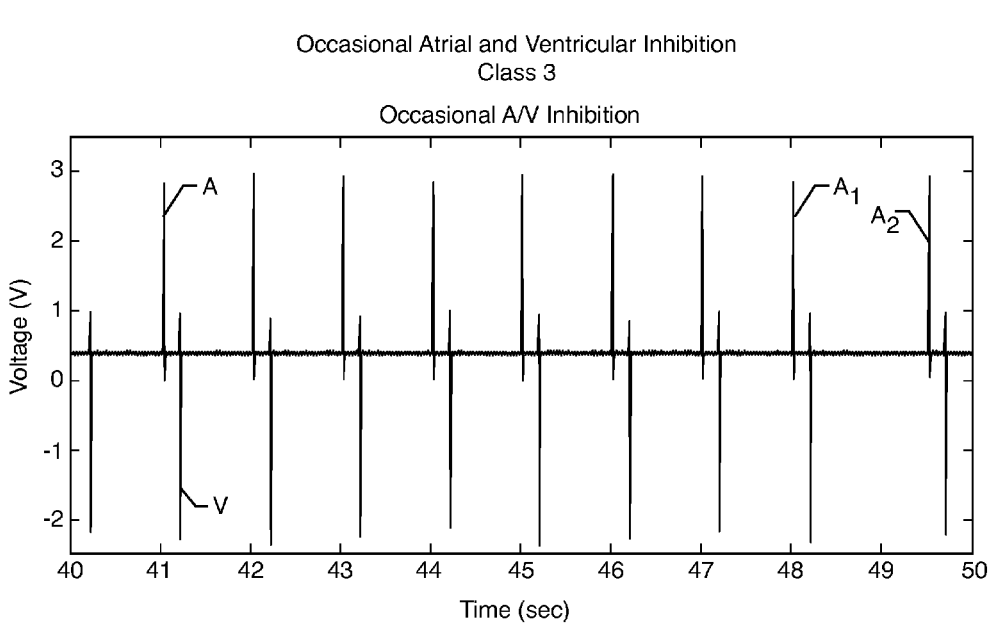
FIG. 17 illustrates a typical Class 3 response—transient (less than 1 second) inhibition.
Figure 18:
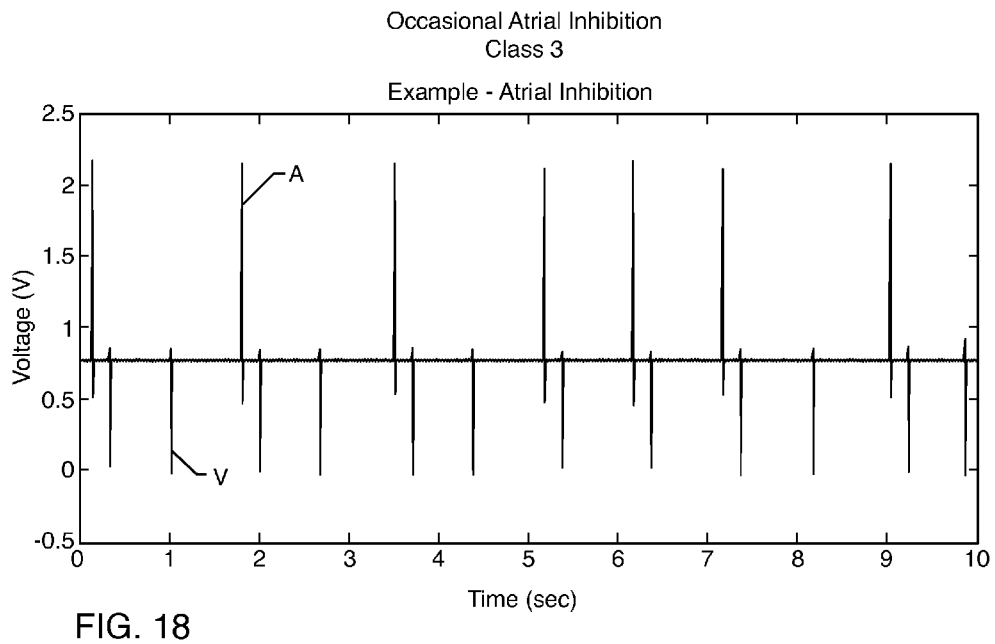
FIG. 18 is an example of an occasional ventricular inhibition and inhibition of every other atrial stimulus output.
Figure 19:
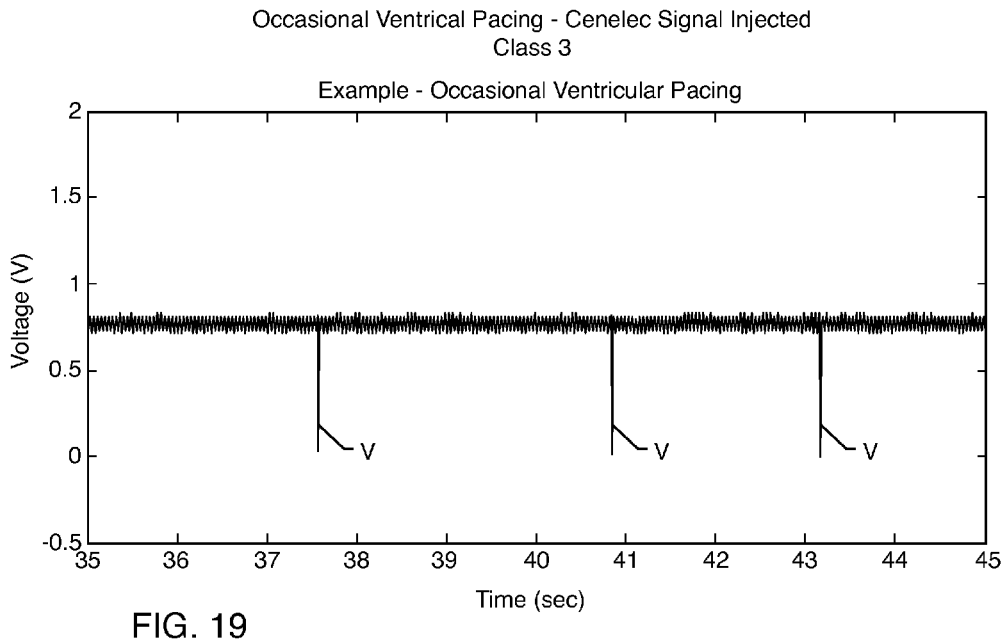
FIG. 19 shows an example of Class 3 occasional ventricular pacing.
Figure 20:
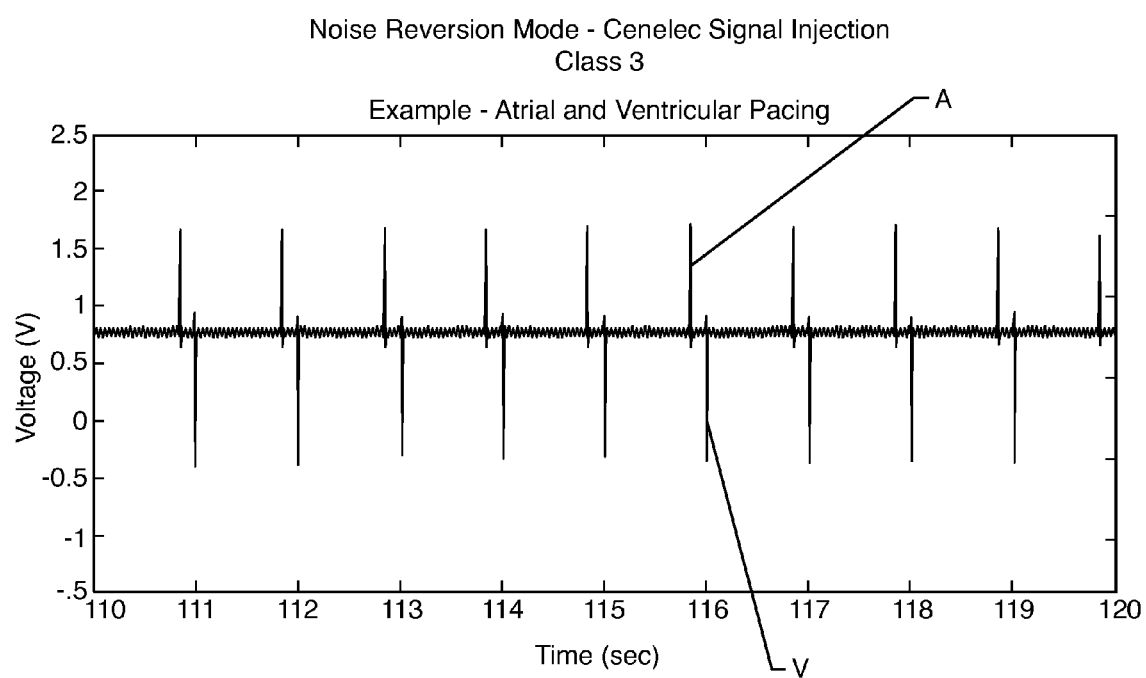
FIG. 20 is an example of a pacemaker that has responded to a CENELEC signal injection by reverting to fixed rate, potentially competitive atrial ventricular stimulus emission.
Figure 21:
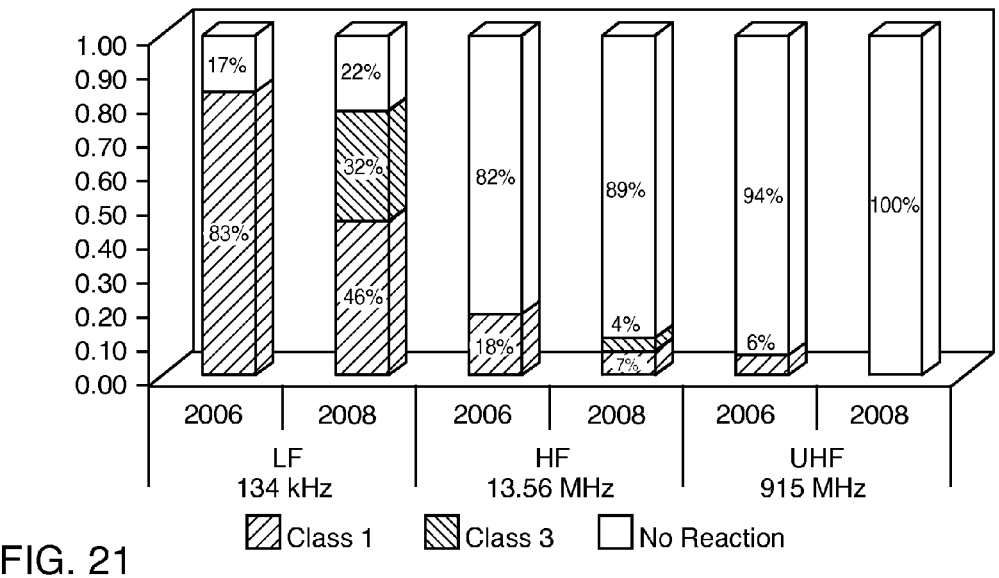
FIG. 21 is a bar graph summarizing the pacemaker data at LF, HF and UHF frequencies.
Figure 22:
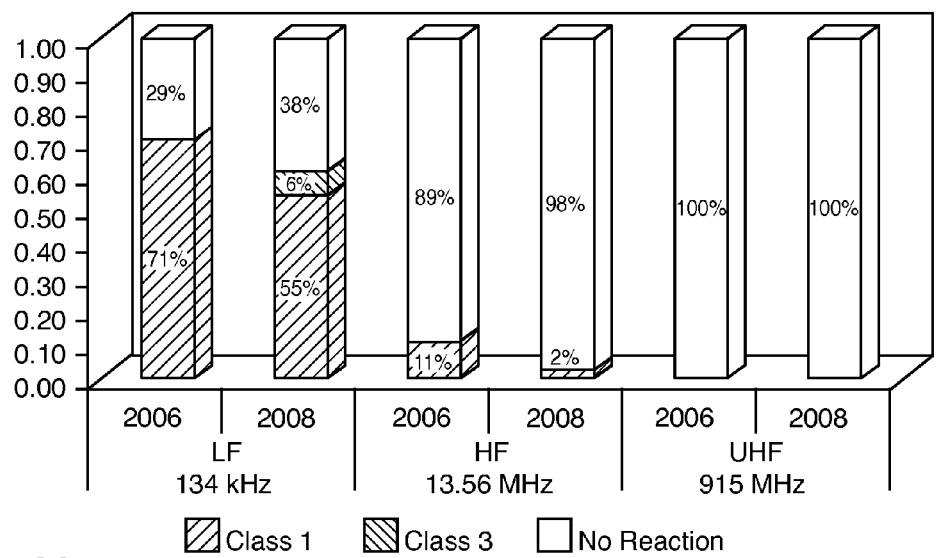
FIG. 22 is a chart similar to FIG. 21, except it is for ICDs.
Figure 23:
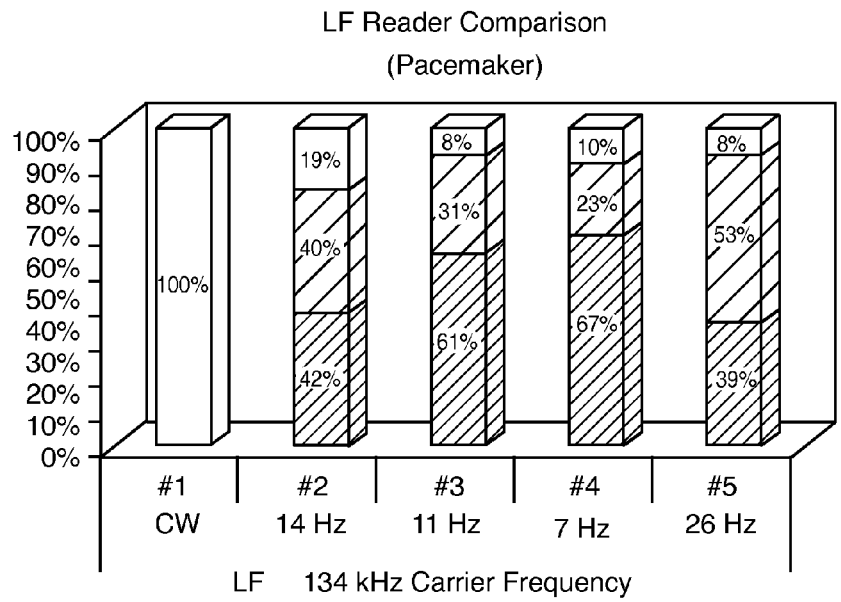
FIG. 23 is a chart showing a comparison of all the different types of LF readers for pacemakers tested.
Figure 24:
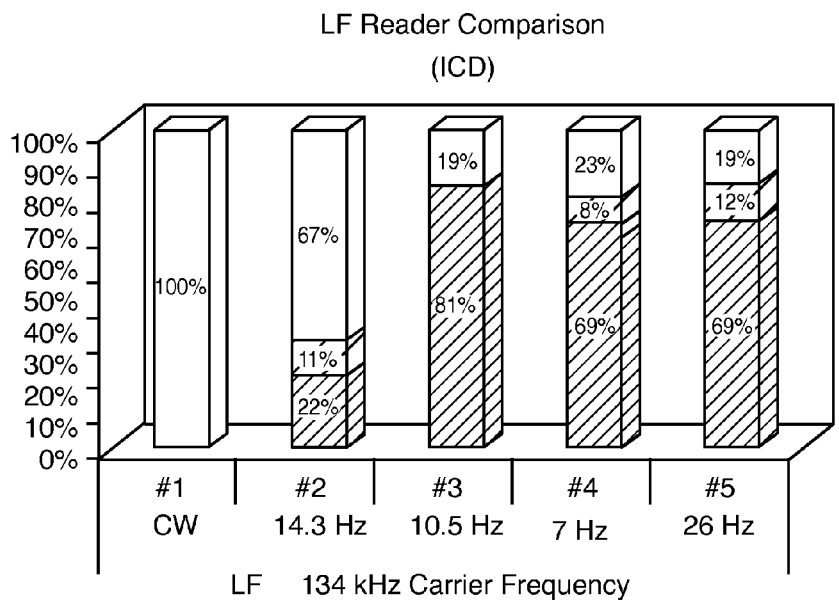
FIG. 24 is a chart similar to FIG. 23, except that it compares LF readers for ICDs.
Figure 25:
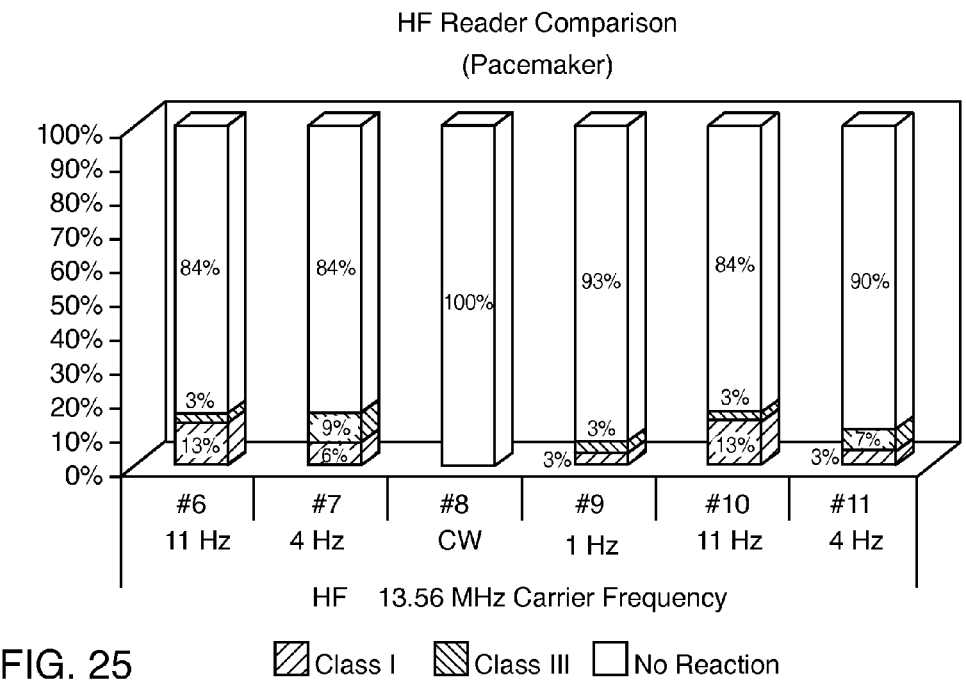
FIG. 25 is a bar graph similar to those shown in FIGS. 23 and 24, however, it is a comparison of pacemaker responses at the 13.56 MHz (HF) carrier frequency.
Figure 26:
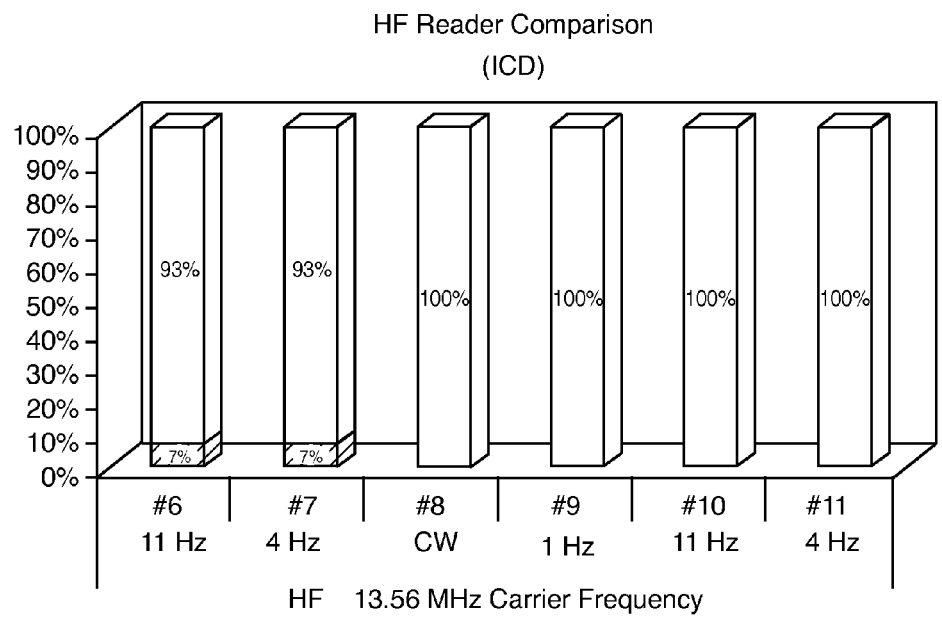
FIG. 26 is a chart similar to FIG. 25 except that it is a comparison of HF readers for ICDs.
Figure 28:
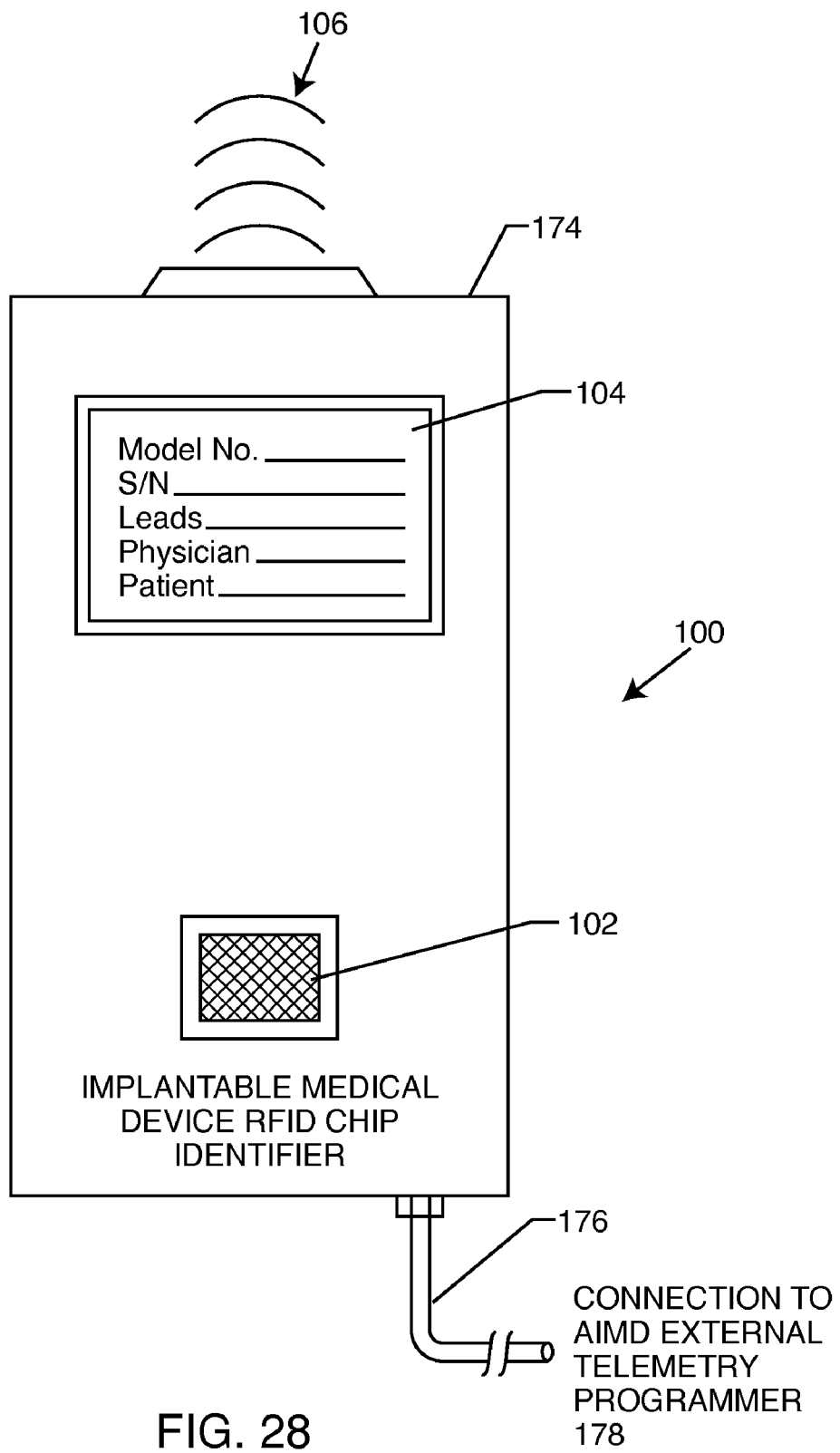
FIG. 28 is a schematic illustration of a novel RFID communicator system embodying the present invention.

FIG. 28 is the top view of a novel hand-held RFID reader/communicator 100 system of the present invention which is connected to an AIMD external telemetry programmer. Shown is a hand-held RFID interrogator 174, push button switch 102 and a screen 104, which could display medical device model number, serial number, type and model number of leads, name and contact information for implanting physician, name and other pertinent information about the patient (with informed patient consent). Since the hand-held interrogator 174 is connected to either a newly designed or prior art AIMD external telemetry programmer 178, the display of medical device model number, serial number and the like need not be on the hand-held unit 174 as shown. Cable 176 is connected to an AIMD external programmer 178. With appropriate software modifications, the external telemetry programmer 178 could also display the information illustrated in window 104 of FIG. 28. It would also be possible to eliminate the push button 102 shown in FIG. 28 and instead use the keyboard of the external telemetry programmer 178 to initiate RFID interrogation. The combination of the hand-held RFID interrogator 174 and its connection 176 to an external AIMD telemetry programmer 178 forms an RFID reader/communicator system 100 of the present invention. The transmit pulses 106 are shown as a series of electromagnetic waves being emanated from the RFID communicator 100. The communicator 100 is integrated into or connected to an AIMD external telemetry programmer which may include a printer, printer interface or computer/network connection for creating a permanent record. This would be advantageous for medical personnel at the scene, for creating accurate medical records and for future reference in case of medical, legal or other delayed concerns. The RFID reader of the present invention need not be hand-held as shown in FIG. 28, but it could be mounted in the AIMD external telemetry programmer itself. In the future it is envisioned that the RFID and telemetry communicating functions will all be part of an integrated single programmer interrogator system, just as current programmers now include electrocardiographic and electrogram functions along with their standard pacing system interrogating and programming functions.

Figure 29:
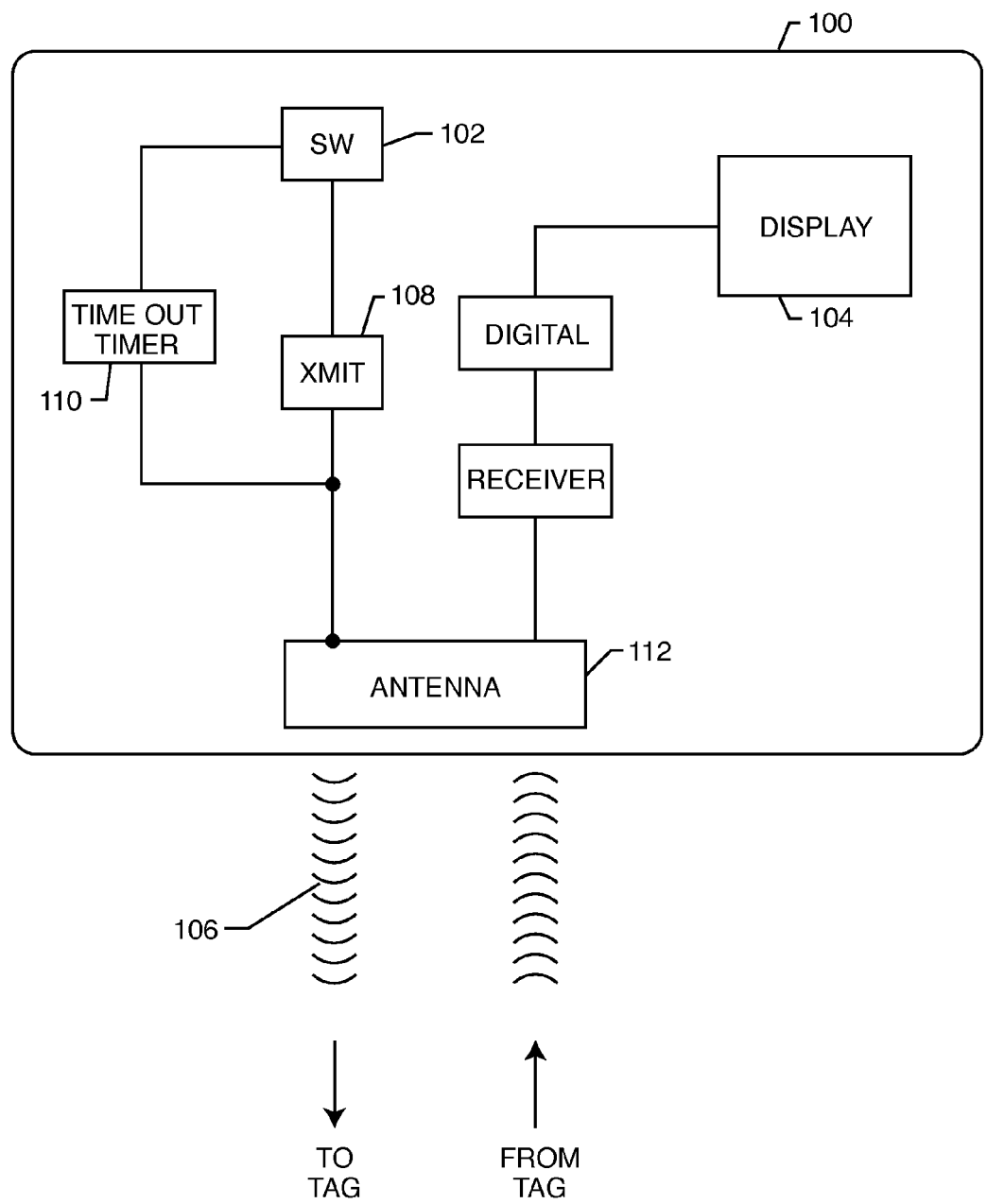
FIG. 29 is a functional block diagram showing a novel application of the present invention.

FIG. 29 is a functional block diagram showing a novel application of the present invention. Shown is the switch SW (102), which can be, but is not limited to, a push button switch like that shown in FIG. 28. In this case, the switch SW (102) would contain special electronic circuitry so it could transmit an electronic pulse 106 for no longer than 5 seconds, or other physiologically safe duration. In a preferred embodiment, the electromagnetic pulse 106 could have a duration or maximum transmit time of no longer than 0.5 seconds combined with a time-out period of 2 seconds or more. Depending on the type of patient AIMD, the transmit time can vary from nanoseconds to several minutes. The transmit duration and time out could be programmable to shorter and longer settings if there were specific physician or regulatory concerns.

For example, for a cardiac pacemaker, limiting transmit time to 0.5 seconds, would, by definition, make it impossible to have a Type 1 or Type 2 response from an implanted cardiac pacemaker or implanted defibrillator. As previously described, dropping of a few paced beats would not be detected by the patient and regardless, would be of no clinical significance. This approach provides an even greater safety margin for ICD compared with bradycardia pacing patient requirements as when implantable defibrillators sense rapid signals that could represent a dangerous ventricular arrhythmia, they begin to charge a high-energy storage capacitor. A final interrogation (sensing of biological signals) is made prior to delivery of the high voltage shock. This entire process takes at least 5 seconds and a progressively longer time as the ICD battery ages. Accordingly, by limiting the transmit pulse of the present invention to less than 5 seconds (preferably less than 500milliseconds), one is guaranteed that no harm can come to the patient from malfunction or inhibition of a pacemaker or triggering of an implantable defibrillator, during transmission of important diagnostic information. It should also be noted that the majority of patients seen in follow-up clinics, are not pacemaker dependent during their visits, and this includes the minority who have complete heart block. A similar corollary is made for all other types of neurostimulators. For example, consider the case of a cochlear implant. If one were to have a patient in an emergency room in a life-threatening situation, the application of the reader of the present invention, would only cause the patient to hear some audible buzzes during the short burst from the RFID reader, As another example, for an epilepsy control stimulator, one or two extra pulses to the brain would be of no clinical significance. The same would be true of a spinal cord stimulator, a vagus cord stimulator, an incontinence (bladder control) stimulator, or the like. Even if the short RF burst from the reader transiently terminated the output of a pain control stimulator, the patient would be without pain suppression stimuli a maximum of only 5 seconds. Therefore the present invention is applicable to all types of active implantable medical devices and is not just limited to pacemakers and implantable defibrillators.

Referring once again to FIG. 29, one can see that there is a timer circuit 110 designed to bypass the RF signal generator 108 within the RFID reader 100. After the transmit pulse 106 is sent by antenna 112, to the RFID tag, which has been implanted inside a human or worn by a person in another RF signal sensitive location, the timer 110 prevents the switch 102 from working again for a predetermined amount of time, for example, at least 2 seconds. Therefore, if the push button switch SW (102) is held down continuously, only a single output sequence is delivered and a second and/or further outputs are suppressed until after the specified novel time-out or delay period(s) has occurred. No matter how long the switch 102 is activated and/or reactivated, the transmitter cannot continue to or continuously transmit an RF or any other type of electromagnetic signal. With applying the present invention to cardiac rhythm management devices, an optimal delay or time-out period would be in the range of 2 seconds, giving the heart, for example, time to revert to its intrinsic stable rhythm before it could be disturbed again by additional dropped beats if the user of the reader were to retransmit. Of course, in patients with pacing capable devices, but without pulse generator dependent rhythms, for example, during normal sinus rhythm, the reader transmissions would have no effect even when the switch was appropriately activated. On the other hand, in ICD patients, whether paced or in a normal intrinsic rhythm, there would always be potential risk during RF reader activation, in particular, if transmission durations were to reach and exceeded ten seconds.

Referring once again to FIG. 28, the RFID reader 100 or the external AIMD telemetry programmer has a transmit button 102. Even if the transmit button 102 is pressed repeatedly, if the transmit time is limited in accordance with the present invention, e.g., to less than 0.5 seconds (500 milliseconds), then, at most, a pacemaker patient will only drop a few heart beats. However, the time-out circuit is equally important. If for some reason the transmit button 102 is pushed over and over again, this could cause a prolonged pacemaker inhibition period which could be potentially pro-arrhythmic or even life-threatening to the patient. The novel time-out circuit of the present invention ensures that the transmit button 102 will not work again for a specified period of time.

For pacemaker and implantable defibrillator applications, the ideal time-out period is based on a number of factors. For a cardiac pacemaker, that has to do with the wide range of human conditions and their particular underlying cardiovascular disease or cardiac hemodynamics. Taking all of this into consideration, the preferred transmit time is 500 milliseconds or less and the preferred time-out period is two seconds or longer. This preferred embodiment is also ideal for implantable cardioverter defibrillators, which in order to deliver therapy, must first detect a dangerous (fast rate) ventricular arrhythmia. If such fast rate ventricular arrhythmia is detected, the ICD high energy internal storage capacitor is charged up. It typically takes several seconds for the battery to charge up the capacitor. Then the ICD reinterrogates to see if the dangerous arrhythmia, or in this case EMI, is still present. If it is, the ICD delivers a high voltage shock. This entire process generally takes longer than 6 seconds. This preferred embodiment also works in general for neurostimulators.

It has been widely described in the literature that when potential patients have a resting heart rate below 40 beats per minute that they become a candidates for a cardiac pacemaker. It is also a fact that almost all pacemakers that are built today are sent out with factory default settings of 60 beats per minute. Of course, this setting can be adjusted through reprogramming by the implanting or follow-up physician (often working in cooperation with the manufacturer's device representative). In certain cases, for world class athletes, vasomotor syncope patients etc the physician may decide to turn down the pacemaker set rate to 50 beats per minute, for example, or even lower. This is because certain athletes find 60 beats per minute to be uncomfortable (rate too fast). In a preferred embodiment of the present invention, the total transmit time of the electromagnetic signal would be limited to 500 milliseconds (0.5 seconds). This would be combined with a time-out period of 2 seconds or more. If one does the math over a full minute, this would mean that a pacemaker dependent patient, who was being paced at 50 beats per minute, would lose a maximum of 10 beats over that full minute or have an effective 40 beats per minute heart rate. This would put the patient right on the edge of the indications for a cardiac pacemaker. However, this still provides a high degree of safety for an athletic patient, since it is well known that athletes can drop to as low as 25 beats per minute before they become dizzy. Accordingly, the preferred embodiment of the present invention would be to limit the total transmit time to 500 milliseconds and the time-out period to a minimum of 2 seconds. This preferred embodiment also works well for ICD and neurostimulator patients.

However, the present invention does not limit the transmit time and time-out period to any specific number. The reason for this is there is great variability in the characteristics of AIMDs, and AIMDs are evolving over time. For example, pacemakers are evolving to have more functions and more lead-based sensors. Accordingly, their EMI characteristics could change over time necessitating that the total transmit time and/or the time-out period be adjusted in the future. In addition, it's quite possible, if not likely, for example, to interrogate a pacemaker implanted in a patient with am RFID reader, then later interrogate a spinal cord stimulator implanted in that same patient with the same RFID reader. This is particularly true for LF chips that may be embedded inside the AIMD housing. The detect range of these RFID readers is typically from 2 to 6 inches maximum. This would place the RFID reader in very close proximity to the AIMD that had an RFID tag associated with it. Accordingly, one could conceive of a reader that was used only for interrogating pacemakers when it was closely held. In this case, it would have to have a more limited transmit time and perhaps a longer time-out period. On the other hand, if one were interrogating a spinal cord stimulator, the transmit time and time-out period would not be nearly as critical because the spinal cord stimulator is not a lifesaving device. In other words, if the patient experienced a few seconds of pain, this would be more preferable than having the heart stop.

The transmit time is, of course, also related to the amount of information that is desired to be either written or retrieved from a tag. Accordingly, in the simplest embodiment, a transmit period of only a few nanoseconds may suffice. This would work in combination with a look-up table that would be built within the reader. In this case, all of the implantable medical device, such as a cardiac pacemaker, would have to transmit would be a two-letter code. This two-letter code would ideally be tied to an Association for the Advancement of Medical Instrumentation (AAMI) standard or International Standards Organization (ISO) standards wherein the manufacturers' look-up tables would be contained. For example, the code A1 could stand for St. Jude Medical. It would only take the tag a few nanoseconds to transmit the code A1. On the other hand, if it were desired that the tag transmit not only manufacture, but in addition, model number, serial number, date of manufacture, name of both the patient and implanting physician and so on, then the data transmission time would increase. Accordingly, in the present invention, the transmission time would be limited, in general, from 1 nanosecond all the way to 2 seconds, and the time-out period can be from a few nanoseconds to a number of minutes. As mentioned, this is very device specific as well. A drug pump will not respond nearly the same way as a cardiac pacemaker, for example. Clearly, from the perspective of emergency room attendants, and in keeping with the large amount of data clinicians now take for granted being downloaded from pacemakers and ICDs, having as much critical data immediately available from implanted RFID tags in an easily interpretable digital format is ideal. Reference manuals are more often than not misplaced just at the time you critically need them.

Figure 30:
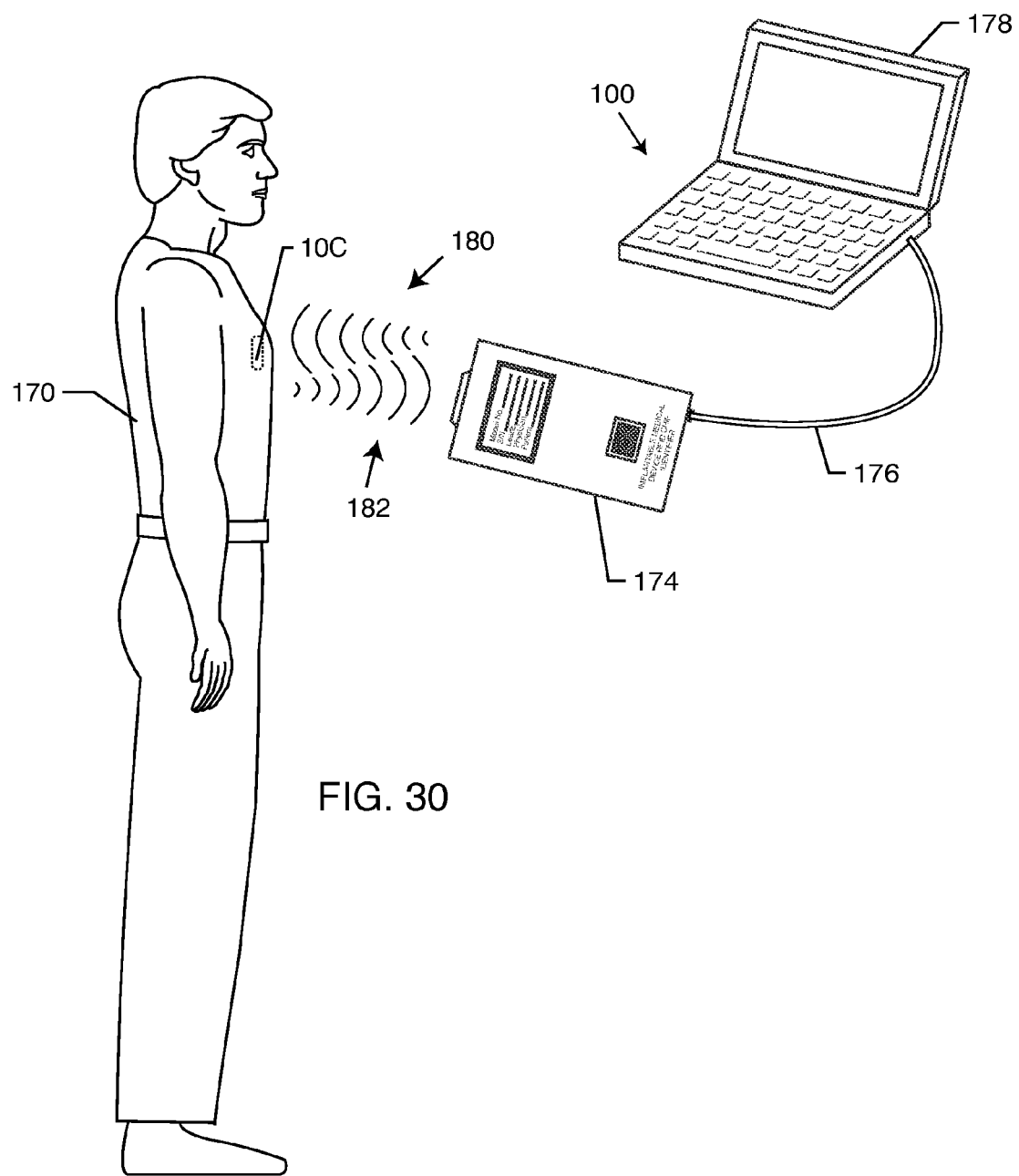
FIG. 30 is a depiction of a patient with an AIMD fitted with an RFID tag communicating with an external interrogator/reader embodying the present invention.

FIG. 30 illustrates a patient 170 with an implanted pacemaker 10C. There is a great need in ambulances, hospital emergency rooms, and other environments to quickly and accurately detect the model number, the serial number and other information about any implanted medical device. This is also very important before certain diagnostic procedures such as MRI. Shown is the communicator unit 174 sending a signal 180 towards the implanted pacemaker 10C and its associated RFID tag (not shown). A return pulse 182 is emitted from the RFID tag which is received by the RFID communicator 174. This information, in turn, is transmitted via cable 176 to the external AIMD telemetry programmer 178. The RFID tag could also be implanted in other locations within the patient's body or even within a special patient ID card or wristband. In an ER setting and elsewhere the RFID communicator 174 could be used for device identification before/or without a standard programmer 178 being available. In addition to the screen for immediately visualizing critical data, a receipt printer like function would be preferred, but with the overall dimensions of 174 being maintained in the typical hand held size range.

In summary, FIG. 30 illustrates yet another scenario in which RFID tags will soon be placed in AIMDs, and readers will deliberately be brought very close to the patient in order to obtain identity information about the AIMD itself. The situation illustrated in FIG. 30 is probably the most dangerous, for a pacemaker or ICD patient. In this example, a very powerful RFID reader is deliberately placed literally right up against the patient's chest in order to retrieve information from the pacemaker or ICD itself and associated leads and other implants. Obviously, it would be highly undesirable if EMI from the reader interrogation signal disrupted the proper operation of the AIMD. Accordingly, it is critical that this RFID reader/interrogator 174 have a limited transmit time and the time-out period of the present invention. The RFID-enabled external telemetry programmer of the present invention is capable of sending out a transmit pulse and receiving return signals from the RFID tags previously described within the patient. In the case where there is no return pulse, in the present invention the display will automatically read, "no tag detected" or something similar. In an emergency room situation, it is expected that as one gets a "no tag detected" reading, one would move the reader very close to the patient's implanted device and attempt to reinterrogate. If one again sees a "no tag detected" display, then one would have to assume that they have an old (legacy) device that does not have an embedded RFID tag. Under these circumstances, one would have to return to the old time-consuming routine of searching around the hospital for an programmer electromagnetically compatible with the implanted medical device.

Figure 31:
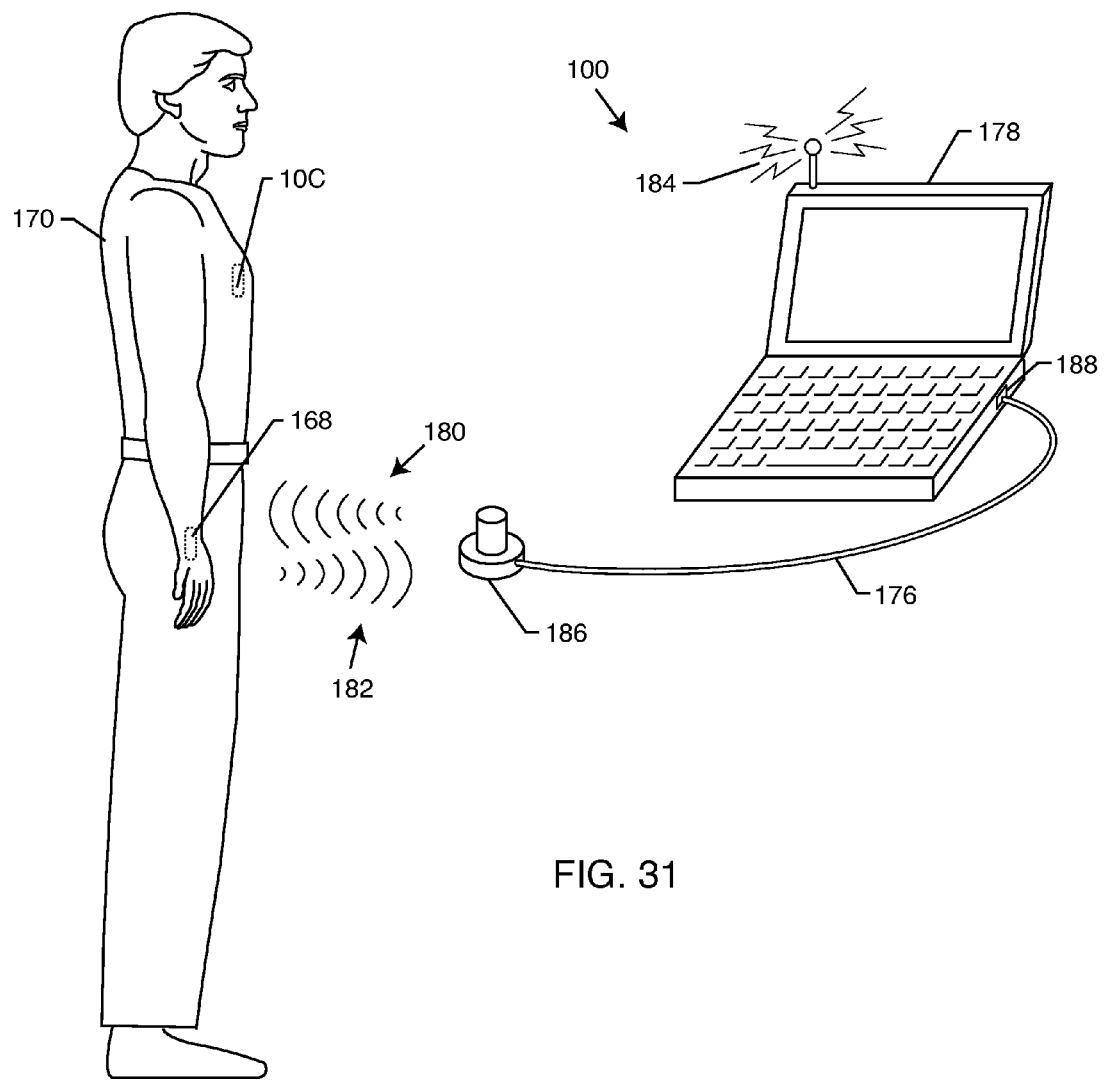
FIG. 31 is similar to FIG. 30, wherein an RFID reader having an interrogator antenna is attached by cable to the AIMD external programmer.

FIG. 31 illustrates an RFID AIMD external programmer 178 in accordance with the present invention. Shown, is an RFID reader and interrogator antenna 186 attached by cable 176 to the enhanced prior art AIMD external programmer 178. In this case, the external programmer 178 is an RF distance telemetry type with an RF antenna 184 although a standard wired programming-receiving wand may also include a RFID transmitter, receiver and RFID chip programmer/data entry functions. If separate, the RFID cable 176 is either hard-wired or plugged in to a pre-existing port 188 of the external telemetry programmer 178. This could be a USB port, a local area network (LAN) port also known as an Rj45 port, a fast Ethernet port, a CAT5, a CAT5e port, a CAT6 port, a fire wire port (also known as IEEE1394i.LINK). A typical prior art port on an AIMD external programmer 178 could also fire wire 400.

Figure 32:
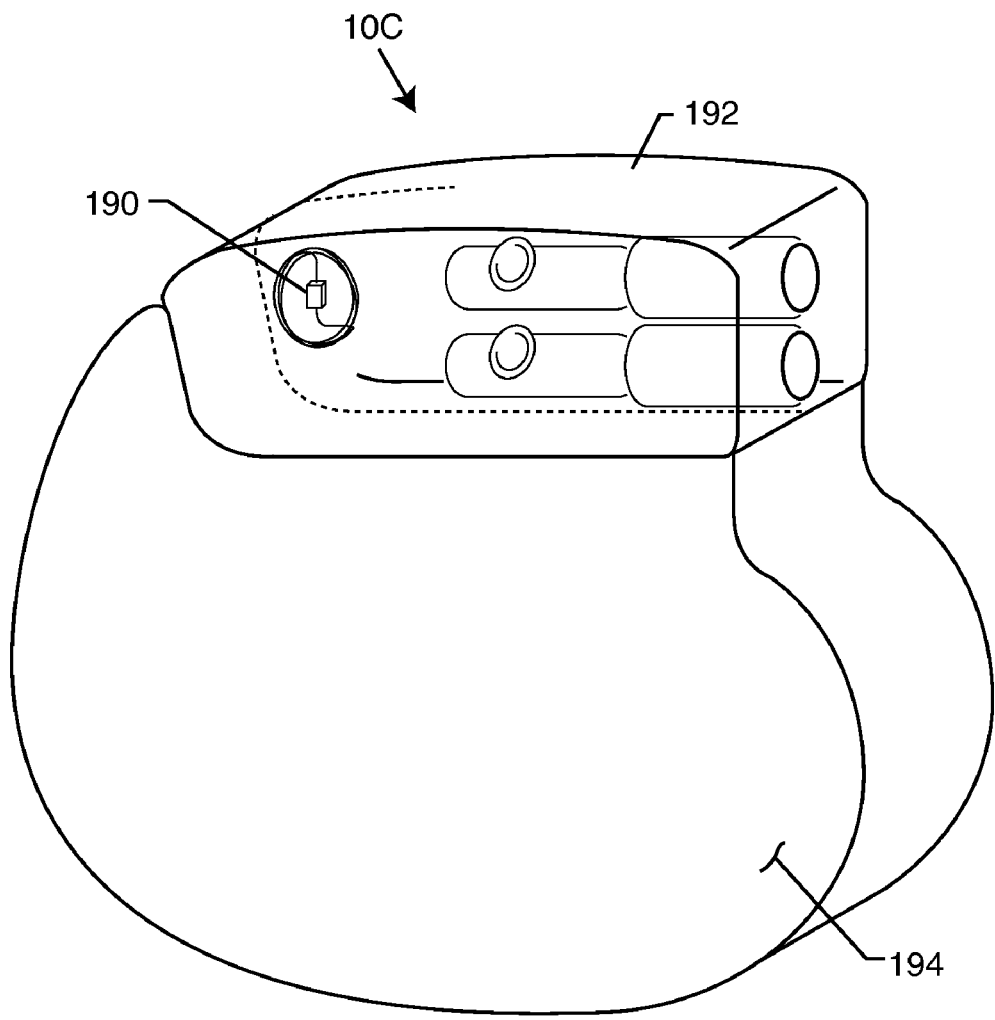
FIG. 32 shows a prior art cardiac pacemaker that includes a hermetically sealed RFID tag and its associated antenna encapsulated in the header.

FIG. 32 illustrates a prior art cardiac pacemaker 10C which has an RFID chip and its associated antenna 190. The RFID chip plus its antenna are known in the art as an RFID tag. There are many other possible locations for the RFID tag 190 other than in the pacemaker header block 192 as shown. The RFID tag 190 could be disposed inside of the AIMD housing 194, or the RFID tag could be surgically implanted or surgically injected anywhere in the human body. The location might be the human wrist 168 as shown in FIG. 31.

Figure 33:
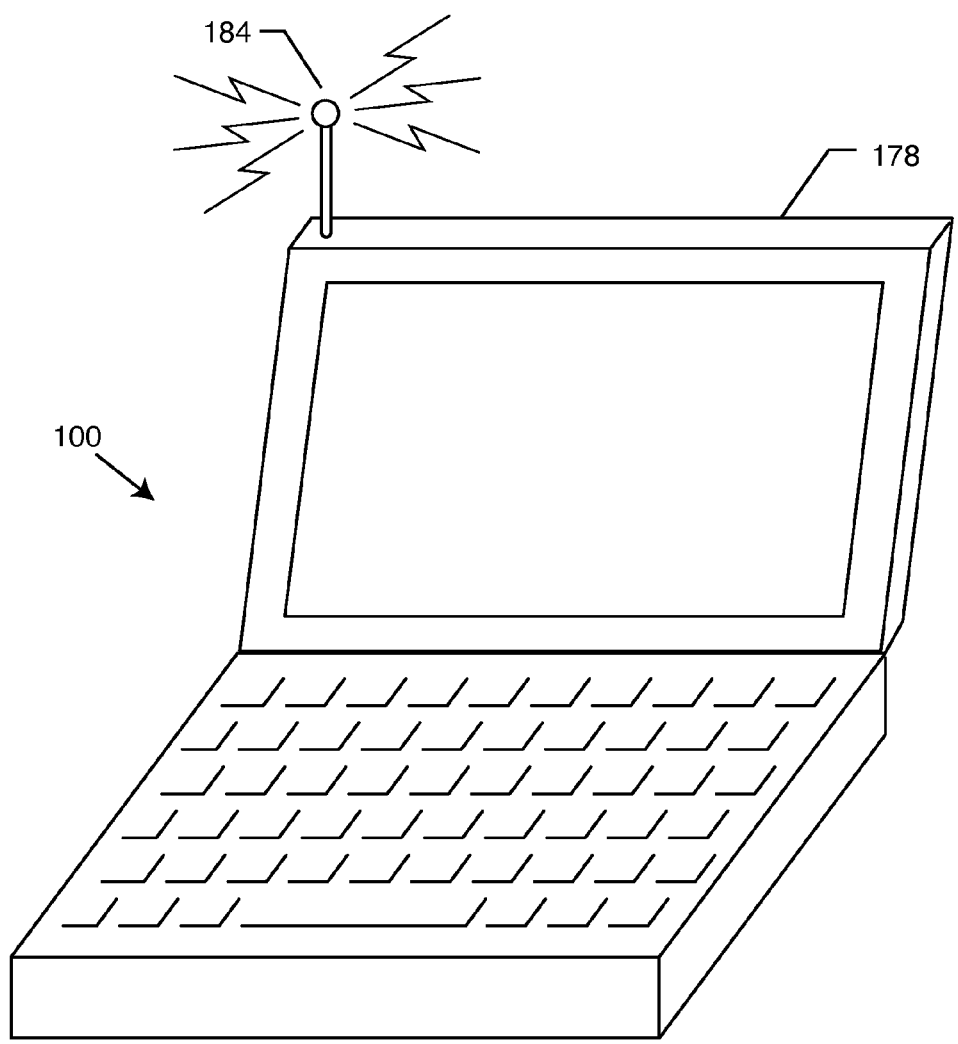
FIG. 33 illustrates an RFID-enabled AIMD external telemetry programmer.

FIG. 33 illustrates an RFID-enabled AIMD external telemetry programmer 178. In this case, the RFID reader/interrogator 174 is entirely built into the AIMD external telemetry programmer 178 as a stand-alone unit. In other words, it derives its power and can communicate data back and forth with the external AIMD programmer 178, but it has its own signal generators and receiving circuitry and has its own built-in antenna 184 for creating its own RFID pulse. It also has its own internal software, including look-up tables. As a practical matter, look-up tables may be an important feature of the present invention. That is, a typical RFID tag may only have 256 bits of information (unless it was a larger type). In other words, saving storage space in the RFID tag chip is important. For example, a designation code could be assigned to each different AIMD manufacturer. For example, Medtronic could be MDT, St. Jude Medical could be STJ, and the like. Accordingly, only the transmission of three letters is required rather than transmitting the full text. In the case of FIG. 31, only the RFID antenna 184 is external to the AIMD external telemetry programmer 178, and all of these look-up table software features would be prewired or pre-programmed into the external AIMD programmer 178. In a preferred embodiment, the programmer, keyboard and soft keys would be interactive with the RFID reader/interrogator antenna 184.

Accordingly, in view of all of the foregoing, it will be appreciated that the present invention relates to design modifications to prior art or newly designed AIMD external telemetry programmers to incorporate an enabled RFID interrogation system either attached to or built within them. In addition, it is important that such RFID interrogation systems have provisions for protecting electronic devices, including medical devices, against RFID-associated electromagnetic interference (EMI). The novel RFID communicators embodied in the present invention include a circuit for limiting the total continuous transmit time of an electromagnetic signal, and a time-out circuit for delaying a subsequent transmission of the electromagnetic signal. By limiting the total continuous transmit time of the electromagnetic signals, in the case of a cardiac pacemaker, only a few heartbeats would be dropped, which is clinically insignificant to the patient, and particularly in comparison to the enhanced safety associated with rapid emergency identification of implanted products and the new and additional advantage of being able to identify leads, adapters and other components. In a preferred embodiment, the total continuous transmit time of the electromagnetic signal is 500 milliseconds or less, and the time-out circuit delays the subsequent transmission of the electromagnetic signal for 2 seconds or more. However, due to the broad applicability of the present invention to various types of transmitters and electronic environments, the total continuous transmit time could be as little as several nanoseconds, and the time-out circuit could delay the subsequent transmission of the electronic signal for up to several minutes or more. The timing details could be programmable plus or minus limited access, lockout features.

Although several embodiments have been described in detail for purposes of illustration, various modifications may be made without departing from the scope and spirit of the invention. Accordingly, the invention is not to be limited, except as by the appended claims.

What is claimed is:
1. A system for communicating with a radio frequency identification (RFID) tag, the system comprising:
   a) an actuatable RF signal generator for transmitting an electromagnetic signal; and b) a time-out circuit, wherein regardless whether an RFID tag is detected, or not, the RF signal generator transmits a first electromagnetic signal having a first limited total continuous transmit time that is not greater than a defined transmit length, followed by an interim period of a defined, manually non-resettable interim length where the time-out circuit renders the interrogator incapable of transmitting the electromagnetic signal, followed by the RF signal generator transmitting a second electromagnetic signal having a second limited total continuous transmit time that is not greater than the defined transmit length, c) wherein no matter how frequently the RF signal generator is actuated, the time-out circuit prevents the second and subsequent transmissions of the electromagnetic signal after a prior electromagne signal has been transmitted from the RF signal generator until the interim period of the defined, manually non-resettable interim length has expired, and d) wherein the first, second and subsequent transmissions of the electromagnetic signal can be less, but not greater than, the defined transmit length.

2. The system of claim 1, wherein the electromagnetic signal comprises an RFID communication signal.

3. The system of claim 1 wherein the electromagnetic signal is selected from the group consisting of an RFID interrogation signal, an RFID tag search signal, an RFID test signal, an RFID read signal, and an RFID write signal.

4. The system of claim 1, wherein the total continuous transmit time for each of the first, second and subsequent transmissions of the electromagnetic signal is no greater than five seconds.

5. The system of claim 1, wherein the time-out circuit prevents transmission of the subsequent electromagnetic, signal for two seconds or more.

6. The system of claim 1 wherein the total continuous transmit time for each of the first, second and subsequent transmissions of the electromagnetic signal is 500 milliseconds or less.

7. The system of claim 1 wherein the time-out circuit is programmable.

8. The system of claim 1, wherein the electromagnetic signal comprises a modulated signal.

9. The system of claim 1, comprising a read-only or a reader/writer device.

10. The system of claim 1, 4 or 5, being communicable with a computer or a computer network.

11. The system of claim 1 wherein the electromagnetic signal is detectable by an RFID tag implanted in a human being.

12. The system of claim 1, wherein the electromagnetic signal is transmittable in the LF (about 125 to about 135 kHz), HF (about 13.56 MHz), VHF (about 433 MHz), and UHF (about 915 MHz) ranges.

13. The system of claim 1, including a switch for selectively actuating the RF signal generator and the time-out circuit.

14. The system of claim 1 comprising a telemetry wand.

15. The system of claim 1 including an electronic database or look-up table.

16. The system of claim 1 including means for changing retrievable information in an RFID tag.

17. A system that is capable of communicating with an active implantable medical device (AIMD), the system comprising:

a) a radio frequency identification (RFID) interrogator, the interrogator comprising:

i) an actuatable circuit for transmitting an electromagnetic signal emanating therefrom; and ii) a time-out circuit, wherein regardless whether an RFID tag is detected, or not, the RF signal generator transmits a first electromagnetic signal having a first limited total continuous transmit time that is not greater than a defined transmit length, followed by an interim period of a defined, manually non-resettable interim length where the time-out circuit renders the interrogator incapable of transmitting the electromagnetic signal, followed by the RF signal generator transmitting a second electromagnetic signal having a second limited total continuous transmit time that is not greater than the defined transmit length, iii) wherein no matter how frequently the circuit for generating the electromagnetic signal is actuated, the time-out circuit prevents the second and subsequent transmissions of the electromagnetic signal after a prior electromagnetic signal has been transmitted from the RF signal generator until the interim period of the defined, manually non-resettable interim length has expired; and b) wherein the first, second and subsequent transmissions of the electromagnetic signal can be less, but not greater than, the defined transmit length; and c) an active medical device; and d) an RFID tag housed inside or supported on the active medical device.

18. The system of claim 17 wherein the RFID tag comprises a read-only or a readable/writable RFID tag.

19. The system of claim 17 wherein the RFID tag comprises an antenna and an electronic micro hip electrically connected to the antenna.

20. The system of claim 17 wherein the RFID tag is associated with an object in close proximity to a patient having an active medical device.

21. The system of claim 17 wherein the RFID tag includes retrievable information relating to one of the group consisting of the active medical device, a patient, and a physician.

22. The system of claim 21 wherein the retrievable information includes information pertaining to magnetic resonance imaging (MRI) compatibility of the active medical device or an associated lead system.

23. The system of claim 21 including means for changing the retrievable information to correspond to changes in characteristics of the active medical device, an associated lead system, or a patient.

24. The system of claim 17 wherein the active medical device comprises any of the following: a cardiac pacemaker, an implantable defibrillator, a congestive heart failure device, a hearing implant, a cochlear implant, a neurostimulator, a carotid sinus stimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, an endovascular catheter, a Bion or a prosthetic device, and component parts thereof, including lead wires, adapters and other implantable accessories, and abandoned leads.

25. The system of claim 20 wherein the object in close proximity to the patient comprises passive medical devices and components thereof, including any of the following: heart valves, stents, screws, plates, hip implants and other orthopedic implants, knee implants, prosthetics, braces, wristbands, necklaces, identification badges or cards, ankle bracelets, or eyeglasses.

26. The system of claim 17 including an electronic database or look-up table enabling communication between the interrogator and the RFID tag.

27. The system of claim 26 wherein the electronic database or look-up table resides in a computer or computer network in communication with the interrogator, or in the interrogator itself.

28. The system of claim 17 wherein the electromagnetic signal is selected from the group consisting of an RFID interrogation signal, an RFID tag search signal, an RFID test signal, an RFID read signal, and an RFID write signal.

29. The system of claim 17 wherein the total continuous transmit time for each of the first, second and subsequent transmissions of the electromagnetic signal is no greater than five seconds.

30. The system of claim 17 wherein the time-out circuit prevents transmission of the subsequent electromagnetic signal for two seconds or more.

31. The system of claim 17 wherein the total continuous transmit time for each of the first, second and subsequent transmissions of the electromagnetic signal is 500 milliseconds or less.

32. The system of claim 17 wherein the time-out circuit for limiting the total continuous transmit time of the first, second and subsequent electromagnetic signals and for limiting the interim period is programmable.

33. The system of claim 17 comprising a read-only or a reader/writer device.

34. The system of claim 17 being communicable with a computer or a computer network.

35. A system for communicating with a radio frequency identification (RFID) tag, the system comprising:
    a) an interrogator, which comprises:
        i) an actuatable RF signal generator for transmitting an electromagnetic signal; and
        ii) a time-out circuit, wherein regardless whether an RFID tag is detected, or not, the RF signal generator transmits a first electromagnetic sign having a first limited total continuous transmit time that is not greater than a defined transmit length, followed by an interim period of a defined, manually non-resettable interim length where the time-out circuit renders the interrogator incapable of transmitting the electromagnetic signal, followed by the RF signal generator transmitting a second electromagnetic signal having a second limited total continuous transmit time that is not greater than the defined transmit length,
        iii) wherein no matter how frequently the RF signal generator is actuated, the time-out circuit prevents the second and subsequent transmissions of the electromagnetic signal after a prior electromagnetic signal has been transmitted from the RF signal generator until the interim period of the defined, manually non-resettable interim length has expired; and
    b) wherein the first, second. and subsequent transmissions of the electromagnetic signal can be less, but not greater than, the defined transmit length; and
    c) means for changing retrievable information in an RFID tag, the retrievable information corresponding to changes in characteristics of an active medical device, an associated lead system, or a patient.

36. The system of aim 35 wherein the electromagnetic signal is selected from the group consisting of an RFID interrogation signal, an RFID tag search signal, an RFID test signal, an RFID read signal, and an RFID write signal.

37. The system of claim 35 wherein the total continuous transmit time for each of the first, second and subsequent transmissions of the electromagnetic signal is no greater than five seconds.

38. The system of claim 35 wherein the time-out circuit prevents transmission of the subsequent electromagnetic signal for two seconds or more.

39. The system of claim 35 wherein the total continuous transmit time for each of the first, second and subsequent transmissions of the electromagnetic signal is 500 milliseconds or less.

40. The system of claim 35 wherein the time-out circuit for limiting the total continuous transmit time of the electromagnetic signal is programmable.

41. The system of claim 35 comprising a read-only or a reader/writer device.

42. The system of claim 35 being communicable with a computer or a computer network.

43. A system for communicating with a radio frequency identification (RFID) tag, the system comprising:
    a) an actuatable RF signal generator for transmitting an electromagnetic signal; and
    b) a time-out circuit, wherein regardless whether an RFID tag is detected, or not, the RF signal generator transmits a first electromagnetic signal having a first limited total continuous transmit time that is not greater than a defined transmit length, followed by an interim period of a defined, manually non-resettable interim length where the time-out circuit renders the interrogator incapable of transmitting the electromagnetic signal, followed by the RF signal generator transmitting a second electromagnetic signal having a second limited total continuous transmit time that is not greater than the defined transmit length,
    c) wherein no matter how frequently the RF signal generator is actuated, the time-out circuit prevents the second and subsequent transmissions of the electromagnetic signal after a prior electromagnetic signal has been transmitted from the RF signal generator until the interim period of the defined, manually non-resettable interim length has expired, and
    d) wherein the total continuous transmit time for each of the first, second and subsequent transmissions of the electromagnetic signal is no greater than five seconds, and
    e) wherein the first, second and subsequent transmissions of the electromagnetic signal can be less, but not greater than, the defined transmit length.

* * * * *

UNITED STATES PATENT AND TRADEMARK OFFICE
CERTIFICATE OF CORRECTION

PATENT NO. : 8,299,899 B2
APPLICATION NO. : 12/874097
DATED : October 30, 2012
INVENTOR(S) : Christine Frysz, Robert Stevenson and Geddes Frank Tyers Page 1 of 1

It is certified that error appears in the above-identified patent and that said Letters Patent is hereby corrected as shown below:

In the Claims

Column 23, line 16 replace the word "electromagne" with "electromagnetic"

Column 26, line 5 replace the word "aim" with "claim"

Signed and Sealed this
Fourteenth Day of May, 2013

Teresa Stanek Rea
*Acting Director of the United States Patent and Trademark Office*